(12) United States Patent
Gabriel

(10) Patent No.: US 9,423,335 B2
(45) Date of Patent: Aug. 23, 2016

(54) INSTRUMENT AND METHOD FOR OPTICAL PARTICLE SENSING

(75) Inventor: Don Gabriel, Carrboro, NC (US)

(73) Assignee: INVITROX, INC., Durham, NC (US)

( * ) Notice: Subject to any disclaimer, the term of this patent is extended or adjusted under 35 U.S.C. 154(b) by 90 days.

(21) Appl. No.: 14/233,874

(22) PCT Filed: Jul. 20, 2012

(86) PCT No.: PCT/US2012/047766
§ 371 (c)(1),
(2), (4) Date: Mar. 31, 2014

(87) PCT Pub. No.: WO2013/013229
PCT Pub. Date: Jan. 24, 2013

(65) Prior Publication Data
US 2014/0234865 A1     Aug. 21, 2014

Related U.S. Application Data

(60) Provisional application No. 61/510,447, filed on Jul. 21, 2011.

(51) Int. Cl.
*G01N 21/47*    (2006.01)
*G01N 15/02*    (2006.01)
(Continued)

(52) U.S. Cl.
CPC ........ *G01N 15/0211* (2013.01); *G01N 15/1434* (2013.01); *G01N 15/1459* (2013.01);
(Continued)

(58) Field of Classification Search
CPC .............. G01N 2015/1493; G01N 2015/1486; G01N 15/0211; G01N 15/14; G01N 15/1434; G01N 15/1456; G01N 15/1459; G01N 15/147; G01N 33/502; G01N 33/5026; G01N 33/5044; G01N 2015/0065; G01N 2015/0084; G01N 2015/03; G01N 2015/1006; G01N 2015/1087; G01N 2500/10
USPC .......... 356/336, 335, 484; 436/63; 422/82.05; 435/808, 7.21; 702/26
See application file for complete search history.

(56) References Cited

U.S. PATENT DOCUMENTS

| | | | |
|---|---|---|---|
| 6,104,490 A | 8/2000 | Trainer | |
| 6,228,652 B1 * | 5/2001 | Rodriguez | ............. G01N 15/14 356/335 |
| 6,525,823 B1 | 2/2003 | Dogariu et al. | |
| 6,710,879 B1 | 3/2004 | Hansen et al. | |
| 6,794,671 B2 | 9/2004 | Nicoli et al. | |

(Continued)

FOREIGN PATENT DOCUMENTS

| | | |
|---|---|---|
| WO | 2006055562 A1 | 5/2006 |
| WO | 2010063455 A1 | 6/2010 |

*Primary Examiner* — Erik B Crawford
(74) *Attorney, Agent, or Firm* — Andrews Kurth LLP; David Bradin

(57) ABSTRACT

Devices for detecting particle sizes and distributions using focused light scattering techniques, by passing a sample through a focused beam of light, are disclosed. In one embodiment, the devices include one or more lasers, whose light is focused into a narrow beam and into a flow cell, and dispersions are passed through the flow cell using hydrodynamic sample injection. In another embodiment, a plurality of lasers is used, optionally with hydrodynamic sample injection. Particles pass through and scatter the light. The scattered light is then detected using scatter and extinction detectors, and, optionally, fluorescence detectors, and the number and size of the particles is determined. Particles in the size range of 0.1 to 10 μm can be measured. Using the device, significantly smaller particles can be detected than if techniques such as EQELS, flow cytometry, and other conventional devices for measuring biological particles.

19 Claims, 6 Drawing Sheets

ISADE Optical Path

(51) Int. Cl.
*G01N 15/14* (2006.01)
*G01N 33/50* (2006.01)
*G01N 15/10* (2006.01)
*G01N 15/00* (2006.01)

(52) U.S. Cl.
CPC .......... *G01N33/502* (2013.01); *G01N 33/5026* (2013.01); *G01N 33/5044* (2013.01); *G01N 2015/008* (2013.01); *G01N 2015/0065* (2013.01); *G01N 2015/0073* (2013.01); *G01N 2015/0084* (2013.01); *G01N 2015/03* (2013.01); *G01N 2015/1006* (2013.01); *G01N 2015/1087* (2013.01); *G01N 2500/10* (2013.01)

(56) References Cited

U.S. PATENT DOCUMENTS

| | | |
|---|---|---|
| 7,127,356 B2 | 10/2006 | Nicoli et al. |
| 7,430,046 B2 | 9/2008 | Jiang et al. |
| 2004/0011975 A1 | 1/2004 | Nicoli et al. |
| 2005/0250095 A1 | 11/2005 | Gabriel |
| 2009/0323061 A1 | 12/2009 | Novotny et al. |
| 2010/0035235 A1 | 2/2010 | Gabriel |
| 2011/0249255 A1 | 10/2011 | Bentien |
| 2012/0135405 A1 | 5/2012 | Toumbas et al. |
| 2012/0202237 A1* | 8/2012 | Sedoglavich ...... G01N 15/1404 435/29 |

* cited by examiner

ISADE Optical Path

INSTRUMENT AND METHOD FOR OPTICAL PARTICLE SENSING

CROSS-REFERENCE TO RELATED APPLICATIONS

This application is a U.S. national phase under the provisions of 35 U.S.C. §371 of International Patent Application No. PCT/US12/47766 filed Jul. 20, 2012, which in turn claims priority of U.S. Provisional Patent Application No. 61/510,447 filed Jul. 21, 2011. The disclosures of such international patent application and U.S. priority provisional patent application are hereby incorporated herein by reference in their respective entireties, for all purposes.

FIELD OF THE INVENTION

This application is generally in the area of single particle optical light scattering devices, and techniques for using them, particularly measure extremely small particles.

BACKGROUND OF THE INVENTION

It is often essential to characterize biological particles by their size, surface condition, states of activation of any surface receptors, distribution, and the like. This information is useful in cell-based assays and other processes that rely upon those characteristics. Additionally, it is useful in certain diagnostic applications to detect known changes of the surface of a biological particle. Accordingly, it can be desirable to detect the surface and monitor changes to the surface in an efficient and accurate manner.

"Electrophoretic Quasi-Elastic Light Scattering" (EQELS) is one method for characterizing biological particles. This method uses electrophoresis that is dependent on the particle's surface charge density to identify and characterize suspended biological particles. EQELS uses cells placed in an electric field, where the surface charge of the particle will determine how that particle moves in the electric field. Monitoring the electrophoretic mobility of the cells provides information useful in distinguishing among different particles in the field. One can screen and optimize drug candidates which interact with the biological particles by comparing the spectra of the particles alone, or bound to the drug candidates.

Coulter counters can also be used to characterize biological particles. These devices are primarily used to count and size cells and other biological particles. The Coulter Counter works by drawing fluid containing the biological particle through a small opening located within a current between two electrodes. As the fluid is drawn through the opening, the biological particles flow through the current and measurably displace a portion of the current. The measurable displacement is translated to a pulse that is digitally processed by the Coulter Counter and translated to allow one to characterize the size and number of biological particles in the fluid.

Flow cytometry can also be used to characterize biological particles. Flow cytometry uses a beam of light, such as a laser, trained on a fluid to characterize, count and optionally sort particles in the fluid. The fluid is focused into a stream, and detectors at the intersection of the light and the fluid stream determine scatter—both forward and side. Additionally, a fluorescent detector may be present to detect fluorescent or fluorescently-tagged particles. One can determine various physical and chemical characteristics of each individual particle by analyzing the detected pattern.

These methods are useful in detecting and characterizing microparticles, including determining the number of particles, density within a fluid medium, size, and surface characteristics of the particle, confirming binding, or lack thereof, and the like. The microparticles are generally in the size of between 0.1 µm and 100 µm. However, developments in technology demand the characterization of smaller biological particles, including, but not limited to, nanoparticles.

The size of biological particles that can be analyzed using currently available technology is limited. Accordingly, there is a need for devices and processes for characterizing biological particles that can detect biological particles of varying sizes, including particles smaller than microparticles, and which can characterize the detected particles with accuracy, quantify the particles and/or monitor the particles. The present invention provides such devices and processes.

SUMMARY OF THE INVENTION

The present invention relates to devices useful for, and methods of detecting sizes and distributions of particles using focused light scattering techniques. The devices use focused light scattering techniques, and can be used, for example, to diagnose disease, identify therapeutic agents, and obtain other useful information about biological particles and/or therapeutic agents in a sample medium. Representative particle sizes that can be measured range from between about 0.1 µm to about 100 µm, more typically in the range of between about 0.1 and about 20 µm.

Briefly, focused light scattering techniques involve passing a sample media through a particular path, where a focused beam of light passes through the sample media. The focused beam is of a size such that a particle in the size range of 0.1 to 10 µm is sufficient to block all of the beam, or a significant enough part of the beam, so that the particle size can be measured.

When there are no particles passing through the pathway of the beam, the beam passes through the media and onto a detector. When a particle, or part of a particle, passes through the beam, the beam is deflected. A diminished amount of light, or no light at all, then reaches the detector, thus indicating that a particle (or part of a particle) has interacted with the beam. The amount of diminished light reaching the detector provides information about the size of the particle. This is repeated as particles in the sample medium pass through the beam, for example, until the sample medium has entirely passed through the beam. Appropriate algorithms then take the information, and the output is a spectrum showing the particle size and particle distribution.

The device includes light from at least one, and, ideally, at least two laser light sources. Where two or more laser light sources are used, they each ideally provide light at different wavelengths. Where two or more light sources are used, they can be passed through a beam splitter, which combines the light beams. The combined light beams pass through a focusing lens, which focuses the light into a narrow beam. The beam is then passed through a flow cell.

Dispersions including particles which are to be counted and sized are passed through a flow cell, where they pass through the focused beam of light. In one embodiment, the solutions are introduced into the flow cell using a hydrodynamic sample injector. When the focused light beam comes into contact with a particle, the light is scattered.

The scattered light is then passed through a spatial filter, such as a circular spatial filter. The filter allows light reflected at certain angles, indicative of light hitting particles of a certain size, to pass through. Ideally, the filter does not permit light to pass through when it has not interacted with a particle. However, a portion of this light can be reflected off of a mirror, which can be a movable mirror, onto a detector (ideally an extinction detector).

The light passing through the spatial filter is then passed through a collimating lens, which focuses the beam from the reflected angles into a straight line. Where one laser is used, the light can then pass through a focusing lens, which then focuses the light into a narrower beam, which is then passed on to a detector. Where two lasers are used, the light can then pass through a second beam splitter, which splits the beam into two beams.

Ideally, the splitter does not change the orientation of one of the beams. That is, one beam proceeds directly through the splitter, and the other is diverted, for example, at a 90 degree angle. In this manner, rather than using a combination of a collimating lens and focusing lens, one of the beams need only be passed through a focusing lens. The other beam may be spread out when it passes through the splitter, in which case it is advantageous to use both a collimating lens and a focusing lens.

The focused beams of light are passed through chromatic filters, which filters out light of a wavelength produced by one of the lasers, and passes light from the wavelength produced by the other of the lasers onto a detector. This way, it is possible to detect light from each of the lasers at separate detectors. Where some of the particles may be labeled, and the label is detectable, for example, by fluorescence, one can thus obtain information about all particles, and about a subset of particles that fluoresces. Those particles which fluoresce are typically those which form a complex with a fluorescently-labeled material, such as a fluorescently-labeled antibody. In one embodiment, a scattered light detector is used to detect light reflected from all particles, and a fluorescence detector is used to detect light reflected from particles that either are fluorescent, or are complexed with fluorescently-labeled materials, such as fluorescently-labeled antibodies.

The device also includes a dynamic monitoring system and method employed to monitor the size and/or number of particles, and, optionally, additional information on a subset of the particles, such as their number and/or size, which fluoresce when complexed to a particular fluorescent molecule, in a single particle optical sizing device as described herein. In one embodiment, the dynamic monitoring system is a computer either physically connected to the device, or connected remotely, for example, using Bluetooth, infrared, or other such technology, and capable of receiving information from the various detectors, as well as software which handles the digital interface with the device, wherein the computer and software are capable of counting particles, sizing particles, and storing information on the number and size of the particles in a given sample based on the information received from the detectors and algorithms that use this information to determine particle size and/or number of particles.

Using focused light scattering techniques, significantly smaller particles can be detected than if techniques such as EQELS, flow cytometry, and other conventional methods of measuring biological particles are used. Mathematical algorithms described herein can enable one to not only detect small particles, but also to determine a range of particle sizes, relative quantities of such particles, and shapes of the particles.

Cells are one type of biological particle that can be detected. The method can be used to determine the presence or absence of a specific type of cell in a given solution. For example, a sample of blood, urine, spinal fluid, and the like can be evaluated for the presence or absence of bacteria, fungi, viruses, and the like. The particle size, and, optionally, particle shape, can also provide information about the specific type of bacteria, fungi or virus.

In one embodiment, suitable information on the particles can be obtained simply by obtaining a spectra using focused light scattering of a sample medium, wherein the particle size and distribution provides sufficient information about the presence or absence of certain biological particles present in the sample medium. For example, specific bacteria, fungi, or viruses can be identified solely on the basis of their size, and liposomal suspensions can be evaluated for agglomeration solely on the basis of the size of the agglomerated particles.

In other embodiments, where there is an interest in determining whether a particular agent forms a complex with a particular type of biological particle, additional information may be required. That is, one can determine the presence or absence of a particular cell type, or an ejected particle from a type of cell, by forming a complex between a) the cell or ejected particle and b) an active agent conjugated to a microparticle or nanoparticle ("conjugate"). The complex has a larger particle size than the cell, the ejected particle, or the conjugate, so the focused light scattering technique can determine whether a complex was formed on the basis of particle size.

The complex can be formed with a labeled material, such as a fluorescently-labeled antibody. In one embodiment, the device includes one or more additional lasers that shine a beam of light at a frequency in which the fluorescently-labeled antibody/antibodies absorb light. Thus, one source of light can be used to count and size the number of particles, and another can be used to determine the number of particles that formed a complex with a desired fluorescently-labeled material.

In some aspects of this embodiment, the biological particle is a cell that expresses a specific receptor, and the techniques permit high throughput screening of putative therapeutic agents that bind to the receptor.

In other aspects of this embodiment, the biological particle comprises cells from a patient, for example, blood cells or cancer cells, and these cells are incubated with putative therapeutic agents. Agents that bind to the cells can potentially be useful as therapeutic agents for the patient. Accordingly, this embodiment provides personalized medicine approaches.

In some of these embodiments, two spectra are taken. The first is taken on the sample media before complex formation, and the second is taken after complex formation, so one can look for the difference in particle size and distribution. However, in other embodiments, where the complex has a known particle size, and all that is required is to show that the complex formed, one can simply incubate the biological particle and the substance which may or may not form a complex with the biological particle, and use focused light scattering techniques to determine whether the complex was formed.

If the sample medium, with the biological particle and the conjugate both present, is passed repeatedly through the focused light scattering detector over a period of time, the kinetics of complex formation can be observed.

If the sample medium is scanned with the biological particle and the conjugate both present, but with different scans taken with differing concentrations of the biological particle and/or conjugate, one can determine additional information, relative to binding affinity, minimum inhibitory concentration, and the like.

If the sample medium includes cells of different sizes, expressing different receptors, then information on the selectivity of a putative therapeutic agent for one receptor over the other can be obtained.

If the agent binding to the cells results in cell rupture, then the efficacy of the active agent can be represented by a decrease in particle (cell) density in the sample medium over time.

Thus, complex formation provides useful information about the biological particle, or the agent bound to the microparticle or nanoparticle. For example, where the cell is a known cell, one can screen putative therapeutic agents for their ability to bind to the cell. Where the therapeutic agent is a known therapeutic agent, one can determine whether a particular cell binds to the therapeutic agent. This information can be useful in identifying personalized medical approaches for a patient.

For example, it is critical to determine in a timely manner whether a cancer patient will respond to a particular therapy. That is, the tumors can grow and metastasize before the physician determines that the patient does not respond to the therapy.

In one embodiment, the microparticles have a particle size in the range of between about 0.1 and 10 μm, and ideally have a relatively consistent amount of active agent bound to them. One way to produce particles with a relatively consistent amount of active agent bound to them is to use dendrimers, where the dendrimers include a known quantity of the active agent. Another way is to produce polymer particles with a) a relatively narrow size distribution, and b) a relatively consistent amount of protected functional groups, so that after the polymers are produced, the protecting groups can be removed, and the functional groups used to conjugate the polymer particles to an active agent.

The active agent can be conjugated with the particle in such a way that the portion of the active agent that is known to be active (i.e., binds a receptor) is not significantly sterically hindered by its conjugation with the particle. In some embodiments, this will involve preparing an analogue of the active agent which includes a further functional group which can be attached to the particle.

In one embodiment, metallic particles, such as gold particles, are used. Because these particles scatter a significant amount of light, they can be conjugated with a specific active agent, and used to identify even small molecules that bind to the agent. That is, the amount of light that the particle scatters is sufficiently large that the binding of the agent to the molecule of interest can be measured, even though the molecule is not within the size range of biological particles that can be measured. Means for conjugating active agents to metallic particles are known to those of skill in the art.

The present invention will be better understood with reference to the following detailed description.

DETAILED DESCRIPTION

Figure 1:
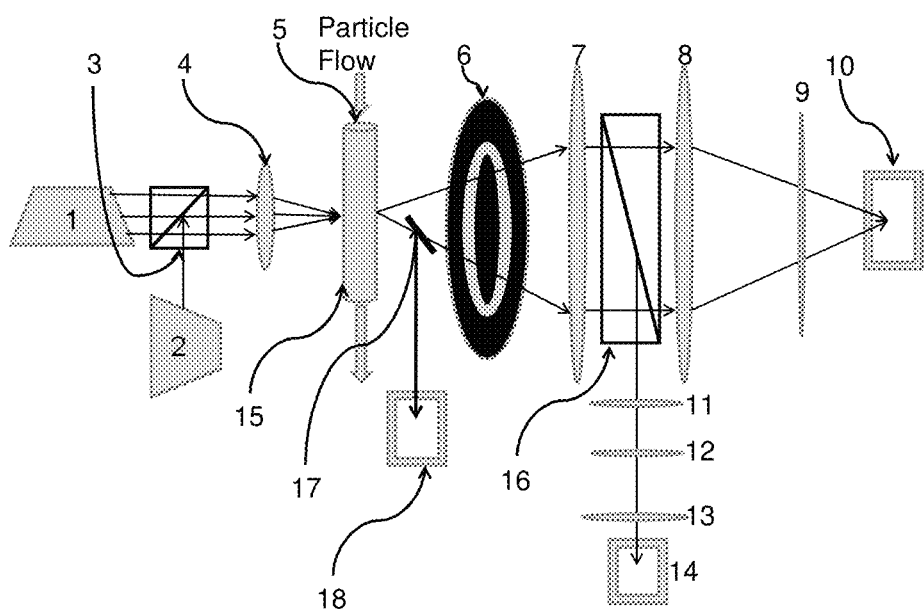
FIG. 1 is a schematic illustration of a single particle optical sizing device, referred to herein as a "surface antigen detection enumerator" light scattering device capable of measuring particles as small as around 0.01 μm in diameter.

The present invention relates to devices for measuring particle size using focused light scattering techniques, and methods for using focused light scattering techniques in biological applications. Focused light scattering techniques provide one with the ability to analyze a fluid and determine the size and number of particles in a given sample and to, optionally, further characterize the particles in the sample. Where the particle is a biological particle, this information can be used to diagnose disease, to conduct high throughput bioassays, and to obtain information for personalized medical treatment.

The methods described herein provide numerous advantages over the previous methods in the art, including the ability to identify and characterize smaller particles, identify particles and determine particle size, number or other characteristics without using fluorescent antibodies or expensive flow cytometry, improving the identification of the initial onset of the change in voltage due, which would improve resolution of the generated spectra, control of particle shearing, and improved information regarding particle shape.

The methods also provide numerous characteristics of the particles being evaluated, including, but not limited to: identifying biological particles and distinguishing them from various cells, quantifying particles, identifying surface epitopes, identifying particle shape, and correlating this information with platelet activation, thrombin production, disease states, and the efficacy of putative therapeutic agents.

The present invention will be better understood with reference to the following definitions.

DEFINITIONS

The term "cell" as used herein refers to any type of cell, including human cells, animal cells (such as swine cells, rodent cells, canine cells, bovine cells, ovine cells and/or equestrian cells) cloned cells, plant cells, or the like. The cells may be blood cells, cultured cells, biopsied cells, or cells that are fixed with a preservative. The cells can be nucleated, such as white blood cells or suspended endothelial cells, or non-nucleated, such as platelets or red blood cells.

The term "focused light scattering" refers to a method for sensing single particles, suspended in a solution, when the solution is passed through a focused beam. When the beam passes through the solution without being scattered by a particle, the beam passes on to a photodetector and the intensity is measured. When the beam is scattered, in whole or in part, by a particle, the intensity of the beam hitting the photodetector is altered. The particle size and concentration can be calculated, for example, using light-extinction, light-scattering detection, or both.

A "focused light scattering device" is a multi-particle optical sensor, which has high sensitivity and responds to relatively concentrated suspensions, uses a relatively narrow light beam to illuminate an optical sensing zone non-uniformly.

As used herein "particles" are small fragments or completely intact biological cells, and related to a living organism when referred to as "biological particles." Intact cells may range in size from about 1 micron to 20 microns. Aggregates of intact cells or fragments of cells may range in size from 2 microns to 100 microns. "Microparticles" are fragments of biological cells or particles that generally range in size from about 0.1 µm to about 0.8 µm, generally 0.1-20 µm. Examples include, but are not limited to blood cells, platelets (1-3 micron), cancer cells (5-15 micron), red blood cells (~7 µm), white blood cells (~5-10 µm), bacteria (~0.5-1 µm), tumors, granulocytes, monocytes, neutrophils, lymphocytes, endothelial cells, stem cells, viruses, and fungi.

"Light extinction" as used herein is a measurement of the absorption and/or scattering of light in an electromagnetic field by particles as they pass through the field. As a particle passes through a field, there is a momentary reduction in the transmitted light intensity due to the light refraction, absorption and/or scattering. Measurement of light extinction by the particles provides additional information regarding the characteristics of the particles. A light extinction spectrum can be generated for each particle.

"Light scattering" occurs when there is a momentary change in the intensity of the incident light caused by the interaction of the incident photons with the particle. In the case on focused scattering device, the intensity of the scattered light reaching the detector is proportional to the size of the particle. Thus, when the particles being characterized are biological particles, the method of light scattering will involve measuring voltage at the detector this will be proportional to the particle size. An exemplary focused light scattering system for detecting biological particles is shown in FIG. 1.

"Nanoparticles" as used herein are particles or biological particles that are generally smaller than 0.1 µm in size. Because of their small size, nanoparticles have a very high surface area to volume ratio. Accordingly, nanoparticles often possess unique physical characteristics. The present invention provides a way to both quantify and monitor nanoparticles, in particular, cellular nanoparticles, which are often believed to be responsible for initiating further biochemical processes in living organisms.

The types of devices that can be used to carry out these diagnostic assays, and methods for performing these assays, are described in more detail below.

I. Focused Light Scattering Devices and Algorithms for Measuring Particle Size and Shape The focused light scattering device includes the following components:

a) one or more lasers which produce beams of laser light, b) a first focusing lens positioned in the path of the beams of laser light, which focusing lens focuses the beams of light to a size wherein a particle with a diameter of about 0.1 µm is sufficient to block all or substantially all of the light, c) a flow cell positioned in the path of the focused light source, wherein the flow cell is capable of receiving a sample medium comprising a dispersion of particles, and passing the sample medium through the focused light source, where light that interacts with one or more of the particles is scattered, and light that does not interact with one or more particles is not scattered, d) a spatial filter, such as a circular spatial filter, positioned in the path of the light, which allows scattered light to pass through, and does not allow light that is not scattered to pass through, e) a collimating lens positioned in the path of light passing through the circular spatial filter, through which scattered light is collimated, f) a second focusing lens positioned in the path of the collimating lens, focusing the light passing through the collimating lens, g) a scatter detector positioned in the path of the focused light passing through the focusing lens, h) a mirror positioned between the flow cell and the circular spatial filter, which mirror reflects a portion of the scattered light, and i) an extinction detector positioned in the path of the reflected scattered light.

Where more than two laser light sources are used, additional focusing lenses, collimating lenses, chromatic filters, and detectors can be used so that each source of laser light can be separated from the others. In one embodiment, the beam splitter used in these embodiments is one that is capable of splitting the beam into multiple beams, rather than just two beams. In another embodiment, a series of beam splitters is used, each of which splits a beam into two beams, so that multiple beams can be obtained.

The device can also include a hydrodynamic flow injector for introducing the sample medium into the flow cell. In one embodiment, the device includes a hydrodynamic flow injector, but only includes one source of laser light. In another embodiment, the device includes two or more sources of laser light, but does not include a hydrodynamic flow injector. In a third embodiment, the device includes two or more sources of laser light and a hydrodynamic flow injector.

In some embodiments, the device includes two or more lasers. In these embodiments, the device further includes a beam splitter that combines the light from the two lasers, and passes the combined light beams through the first focusing lens. In these embodiments, the device further includes a second beam splitter positioned between the collimating lens and the second focusing lens, splitting the beam into two beams, wherein one of the beams is not diverted from its original path toward the second focusing lens, and the other of the beams is diverted from its original path toward the second focusing lens toward a second path.

In order to distinguish between light from the different laser, so that light from only one laser passes through to a given detector, chromatic filters are used to block out light from one or the other of the lasers before the light impinges on a detector. For example, a first chromatic filter can be positioned between the second focusing lens and the scatter detector, which chromatic filter permits light from one of the laser beams to pass through, and which does not permit light from the other of the laser beams to pass through, to the scatter detector. A second collimating lens can be positioned along the second path, which lens collimates the diverted light beam. A focusing lens can be positioned in the path of light passing through the second collimating lens. A second chromatic filter can be positioned in the path of light passing through the focusing lens, which second chromatic filter permits light from the laser beam that did not pass through the first chromatic filter to pass through. A detector, for example, a fluorescence detector, can be positioned in the path of the light passing through the second chromatic filter.

The device also includes a dynamic monitoring system and method employed to monitor the size and/or number of particles, and, optionally, additional information on a subset of the particles, such as their number and/or size, which fluoresce when complexed to a particular fluorescent molecule, in a single particle optical sizing device as described herein. In one embodiment, the dynamic monitoring system is a computer either physically connected to the device, or connected remotely, for example, using Bluetooth, infrared, or other such technology, and capable of receiving information from the various detectors, as well as software which handles the digital interface with the device, wherein the computer and software are capable of counting particles, sizing particles, and storing information on the number and size of the particles in a given sample based on the information received from the detectors and algorithms that use this information to determine particle size and/or number of particles.

The monitoring system includes a data acquisition module operatively coupled to the one or more detectors, and (iii) a processing and display unit operatively coupled to the data acquisition module for determining the size and/or number of particles in a given sample and responsively outputting a graphical representation of the size and/or number of the particles in the sample. The data acquisition module uses the data obtained from the detectors in the single particle optical sensing device described herein, and an algorithm which correlates the data to the size and/or number of particles in the sample medium.

The processing and display unit that is coupled to the data acquisition module may utilize any suitable processing means, e.g., a general purpose programmable digital computer or central processing unit (CPU) including memory and processor components. The processor may be arranged to communicate with the memory by means of an address/data bus, and can be constituted by a commercially available or custom microprocessor. The memory can include, without limitation, devices of varied type, such as cache, ROM, PROM, EPROM, EEPROM, flash memory, SRAM, and DRAM.

The memory may include several categories of software and data used in the data processing system: the operating system; the application programs; the input/output (I/O) device drivers and the data. The data may include a database of known profiles of particle sizes, for example, a reference library of the size of platelets, bacteria, viruses, fungi, cancer cells, stem cells, and complexes of the cells with various molecules, including fluorescently-labeled molecules, such as fluorescently-labeled antibodies, and the like.

It will be appreciated that the operating system in the processing and display unit can be of any suitable type for use with a data processing system. Illustrative examples of operating systems that can be usefully employed include, without limitation, OS/2, AIX, OS/390 or System390 (International Business Machines Corporation, Armonk, N.Y.), Windows CE, Windows NT, Windows95, Windows98, Windows2000, or WindowsXP (Microsoft Corporation, Redmond, Wash.), Unix or Linux or FreeBSD, Palm OS from Palm, Inc., Mac OS (Apple Computer, Inc.), LabView or proprietary operating systems.

The I/O device drivers typically include software routines accessed through the operating system by the application programs to communicate with devices such as I/O data port(s), data storage and certain components of the memory. The application programs are illustrative of the programs that implement the various features of the system and can suitably include one or more applications that support analysis of the data. The data represent the static and dynamic data used by the application programs, the operating system, the I/O device drivers, and other software programs that may reside in the memory.

Any configuration of the processor capable of carrying out the operations for the methodology of the invention can be advantageously employed.

The I/O data port of the processing and display unit can be used to transfer information between the processing and display unit and another computer system or a network (e.g., the Internet) or to other devices controllable by the processor.

The processing and display unit optionally, but ideally, includes a display for graphically outputting information on the size and/or number of particles in a sample, in the form of a representation of the sample being assayed and the size and/or number of particles in the sample. This representation may be a graphic depiction, in which the size and/or number of particles are schematically depicted in a graphical output, as a two-dimensional column listing the size and/or number of particles, and the like. Such type of depictions can provide an intuitive and readily visually perceptible indication of the size and/or number of particles in the sample.

Where the dynamic monitoring system is a computer, which is either physically connected to the device, or capable of receiving information remotely, for example, via Bluetooth or infrared, the computer is capable of receiving information from the various detectors. The computer also includes software which handles the digital interface with the device. The computer and software are capable of counting particles, sizing particles, and storing information on the number and size of the particles in a given sample based on the information received from the detectors. The types of algorithms used to relate information from the various detectors to particle size and/or particle number are described in more detail below.

An exemplary apparatus useful for performing the methods described herein is disclosed in U.S. Patent Application Publication No. 20040011975, the contents of which are hereby incorporated by reference in its entirety. The apparatus is described therein is useful in performing particle analysis using focused light scattering techniques. However, as described herein, other similar apparatus can be employed, including detectors for focused light scattering and/or light extinction.

The principal defining characteristic of the focused light scattering method described in U.S. Patent Publication No. 20070010974, the contents of which are hereby incorporated by reference, is not simply a significant reduction in the size of the illuminated area, $A_O$, resulting in a significant reduction in $V_{OSZ}$ and improvement in sensitivity. Rather, it concerns the nature of the illuminating beam and the resulting OSZ thereby defined.

The term "focused light scattering" refers to a method for sensing single particles, suspended in a solution, when the solution is passed through a focused beam. When the beam passes through the solution without being scattered by a particle, the beam passes on to a photodetector and the intensity is measured. When the beam is scattered, in whole or in part, by a particle, the intensity of the beam hitting the photodetector is altered. The particle size and concentration can be calculated, for example, using light-extinction, light-scattering detection, or both.

In one embodiment, the beam is produced by a laser. The laser beam interacts with the particles, and produces scattered light when the laser beam interacts with a particle. In one aspect of this embodiment, the apparatus includes two or more different lasers, which can give off light at two or more different wavelengths, and/or which can interact with the particles at different angles. The use of light at different wavelengths can enable one to identify specific epitopes. Particles can interact with specific molecules, including fluorescently-labeled molecules, and the fluorescence can be detected using a laser with light at a predetermined wavelength that interacts with the fluorescent label. The use of more than two lasers can enable the use of two or more fluorescent labels, which labels fluoresce at different wavelengths. This technique is described in more detail below.

A beam of light (usually laser light) of a single wavelength is directed onto a hydrodynamically-focused stream of fluid that includes the platelets. A number of detectors are aimed at the point where the stream passes through the light beam. In one aspect of this embodiment, one detector is in line with the light beam (Forward Scatter or FSC) and one or more detectors are perpendicular to it, including Side Scatter or SSC detectors and one or more fluorescent detectors. Each suspended platelet passing through the beam scatters the ray, and fluorescent chemicals either present within the platelet or attached to the platelet are excited into emitting light at a longer wavelength than the light source. This combination of scattered and fluorescent light is picked up by the detectors, and, by analyzing fluctuations in brightness at each detector (one for each fluorescent emission peak), it is then possible to derive various types of information about the physical and chemical structure of each individual platelet.

Thus, in some embodiments of the apparatus described herein, there are three or more detectors. For example, one can include one detector for extinction [used to measure particles with a size >0.7 microns], one for scattered light [used to measure particles with a size in the range of 0.15 to 0.7 microns] and one or more for fluorescence [used for phenotyping].

The sources of light can include lamps (i.e., mercury, xenon); high-power water-cooled lasers (i.e., argon, krypton, dye laser); low-power air-cooled lasers (i.e., argon (488 nm), red-HeNe (633 nm), green-HeNe, HeCd (UV)); diode lasers (i.e., blue, green, red, violet). The detectors can convert fluorescence signals from light into electrical signals that can be processed by a computer.

The process of collecting data from samples is termed "acquisition." Acquisition is typically mediated by a computer physically connected to the apparatus, and the software which handles the digital interface with the apparatus. The software is capable of adjusting parameters (i.e. voltage, compensation, etc.) for the sample being tested, and also assists in displaying initial sample information while acquiring sample data to insure that parameters are set correctly. An interactive database can allow the apparatus to be used in applications for both clinical and research purposes. A wide variety of analysis software and fluorescently-labeled antibodies has been developed, and are well known to those of skill in the art.

The apparatus can include multiple lasers (between 2 and 5, typically between two and four) and fluorescence detectors (typically between 2 and 18, more typically between 2 and 10). Increasing the number of lasers and detectors allows for multiple antibody labeling, and can more precisely identify a target population by their phenotypic markers.

Gating

The data generated by the apparatus can be plotted in a single dimension, in two dimensions, or even in three dimensions. The regions on these plots can be sequentially separated, based on fluorescence intensity, by creating a series of subset extractions, termed "gates." Specific gating protocols exist for diagnostic and clinical purposes especially in relation to hematology.

The plots are often made on logarithmic scales. Because different fluorescent dyes' emission spectra overlap, signals at the detectors have to be compensated electronically as well as computationally. Data accumulated using the apparatus can be analyzed using software, e.g., Flowjo, FCS Express, VenturiOne or CellQuest Pro. Data analysis can be performed on a separate computer, if desired.

Computational Analysis

Automated population identification using computational methods can be used as an alternative to traditional gating strategies. Automated identification systems can potentially help find rare and/or hidden populations. Representative automated methods include FLOCK in Immunology Database and Analysis Portal (ImmPort), FLAME in GenePattern and flowClust, in Bioconductor.

Fluorescent Labels

A wide range of fluorophores can be used as labels in flow cytometry. Fluorophores, or simply "fluors", are typically attached to an antibody that recognizes a target feature, epitope, on or in the cell; they may also be attached to a chemical entity with affinity for the cell membrane or another cellular structure. Each fluorophore has a characteristic peak excitation and emission wavelength, and the emission spectra of different labels often overlap. Consequently, the combination of labels which can be used depends on the wavelength of the lamp(s) or laser(s) used to excite the fluorochromes and on the detectors available (Loken M R (1990). Immunofluorescence Techniques in Flow Cytometry and Sorting (2nd ed.). Wiley. pp. 341-53). The maximum number of distinguishable fluorescent labels is thought to be 17 or 18, and this level of plexy necessitates laborious optimization to limit artifacts, as well as complex deconvolution algorithms to separate overlapping spectra (Ornatsky, O.; Bandura, D.; Baranov, V.; Nitz, M.; Winnik, M. A.; Tanner, S. (2010). "Highly multiparametric analysis by mass cytometry". Journal of Immunological Methods 361 (1-2): 1-20)

Quantum dots are sometimes used in place of traditional fluorophores because of their narrower emission peaks.

The fluorescent labels can be used, for example, to determine the degree of protein expression and localization, the existence of any protein modifications or intracellular antigens (various cytokines, secondary mediators, etc.), membrane fluidity, platelet viability, and platelet adherence.

Representative fluorescent labels are provided below:

| Probe | Ex (nm) | Em (nm) |
| --- | --- | --- |
| Hydroxycoumarin | 325 | 386 |
| Aminocoumarin | 350 | 445 |
| Methoxycoumarin | 360 | 410 |
| Cascade Blue | (375); 401 | 423 |
| Pacific Blue | 403 | 455 |
| Pacific Orange | 403 | 551 |
| Lucifer yellow | 425 | 528 |
| NBD | 466 | 539 |
| R-Phycoerythrin (PE) | 480; 565 | 578 |
| PE-Cy5 conjugates | 480; 565; 650 | 670 |
| PE-Cy7 conjugates | 480; 565; 743 | 767 |
| Red 613 | 480; 565 | 613 |
| PerCP | 490 | 675 |
| TruRed | 490, 675 | 695 |
| FluorX | 494 | 520 |
| Fluorescein | 495 | 519 |
| BODIPY-FL | 503 | 512 |
| TRITC | 547 | 572 |
| X-Rhodamine | 570 | 576 |

-continued

| Probe | Ex (nm) | Em (nm) |
|---|---|---|
| Lissamine Rhodamine B | 570 | 590 |
| Texas Red | 589 | 615 |
| Allophycocyanin (APC) | 650 | 660 |
| APC-Cy7 conjugates | 650; 755 | 767 |
| Alexa Fluor 350 | 343 | 442 |
| Alexa Fluor 405 | 401 | 421 |
| Alexa Fluor 430 | 434 | 540 |
| Alexa Fluor 488 | 499 | 519 |
| Alexa Fluor 500 | 503 | 525 |
| Alexa Fluor 514 | 517 | 542 |
| Alexa Fluor 532 | 530 | 555 |
| Alexa Fluor 546 | 561 | 572 |
| Alexa Fluor 555 | 553 | 568 |
| Alexa Fluor 568 | 579 | 603 |
| Alexa Fluor 594 | 591 | 618 |
| Alexa Fluor 610 | 610 | 629 |
| Alexa Fluor 633 | 632 | 648 |
| Alexa Fluor 647 | 652 | 668 |
| Alexa Fluor 660 | 663 | 691 |
| Alexa Fluor 680 | 680 | 702 |
| Alexa Fluor 700 | 696 | 719 |
| Alexa Fluor 750 | 752 | 776 |
| Alexa Fluor 790 | 782 | 804 |
| Cy2 | 489 | 506 |
| Cy3 | (512); 550 | 570; (615) |
| Cy3B | 558 | 572; (620) |
| Cy3.5 | 581 | 594; (640) |
| Cy5 | (625); 650 | 670 |
| Cy5.5 | 675 | 694 |
| Cy7 | 743 | 767 |
| DyLight 350 | 353 | 432 |
| DyLight 405 | 400 | 420 |
| DyLight 488 | 493 | 518 |
| DyLight 549 | 562 | 576 |
| DyLight 594 | 593 | 618 |
| DyLight 633 | 638 | 658 |
| DyLight 649 | 654 | 673 |
| DyLight 680 | 692 | 712 |
| DyLight 750 | 752 | 778 |
| DyLight 800 | 777 | 794 |
| Hoechst 33342 | 343 | 483 |
| DAPI | 345 | 455 |
| Hoechst 33258 | 345 | 478 |
| SYTOX Blue | 431 | 480 |
| Chromomycin A3 | 445 | 575 |
| Mithramycin | 445 | 575 |
| YOYO-1 | 491 | 509 |
| Ethidium Bromide | 493 | 620 |
| Acridine Orange | 503 | 530/640 |
| SYTOX Green | 504 | 523 |
| TOTO-1, TO-PRO-1 | 509 | 533 |
| Thiazole Orange | 510 | 530 |
| Propidium Iodide (PI) | 536 | 617 |
| LDS 751 | 543; 590 | 712; 607 |
| 7-AAD | 546 | 647 |
| SYTOX Orange | 547 | 570 |
| TOTO-3, TO-PRO-3 | 642 | 661 |
| DRAQ5 | 647 | 681, 697 |
| Indo-1 | 361/330 | 490/405 |
| Fluo-3 | 506 | 526 |
| DCFH | 505 | 535 |
| DHR | 505 | 534 |
| SNARF | 548/579 | 587/635 |
| Y66H | 360 | 442 |
| Y66F | 360 | 508 |
| EBFP | 380 | 440 |
| EBFP2 | 383 | 448 |
| Azurite | 383 | 447 |
| GFPuv | 385 | 508 |
| T-Sapphire | 399 | 511 |
| TagBFP | 402 | 457 |
| Cerulean | 433 | 475 |
| mCFP | 433 | 475 |
| ECFP | 434 | 477 |
| CyPet | 435 | 477 |
| Y66W | 436 | 485 |
| dKeima-Red | 440 | 616 |

-continued

| Probe | Ex (nm) | Em (nm) |
|---|---|---|
| mKeima-Red | 440 | 620 |
| TagCFP | 458 | 480 |
| AmCyan1 | 458 | 489 |
| mTFP1 (Teal) | 462 | 492 |
| S65A | 471 | 504 |
| Midoriishi-Cyan | 472 | 495 |
| Wild Type GFP | 396, 475 | 508 |
| S65C | 479 | 507 |
| TurboGFP | 482 | 502 |
| TagGFP | 482 | 505 |
| TagGFP2 | 483 | 506 |
| AcGFP1 | 484 | 510 |
| S65L | 484 | 510 |
| Emerald | 487 | 509 |
| S65T | 488 | 511 |
| EGFP | 488 | 507 |
| Azami-Green | 492 | 505 |
| ZsGreen1 | 493 | 505 |
| Dronpa-Green | 503 | 518 |
| TagYFP | 508 | 524 |
| EYFP | 514 | 527 |
| Topaz | 514 | 527 |
| Venus | 515 | 528 |
| mCitrine | 516 | 529 |
| YPet | 517 | 530 |
| TurboYFP | 525 | 538 |
| PhiYFP | 525 | 537 |
| PhiYFP-m | 525 | 537 |
| ZsYellow1 | 529 | 539 |
| mBanana | 540 | 553 |
| Kusabira-Orange | 548 | 559 |
| mOrange | 548 | 562 |
| mOrange2 | 549 | 565 |
| mKO | 548 | 559 |
| TurboRFP | 553 | 574 |
| tdTomato | 554 | 581 |
| DsRed-Express2 | 554 | 591 |
| TagRFP | 555 | 584 |
| DsRed monomer | 557 | 592 |
| DsRed2 ("RFP") | 563 | 582 |
| mStrawberry | 574 | 596 |
| TurboFP602 | 574 | 602 |
| AsRed2 | 576 | 592 |
| mRFP1 | 584 | 607 |
| J-Red | 584 | 610 |
| mCherry | 587 | 610 |
| HcRed1 | 588 | 618 |
| mKate2 | 588 | 633 |
| Katushka (TurboFP635) | 588 | 635 |
| mKate (TagFP635) | 588 | 635 |
| TurboFP635 | 588 | 635 |
| mPlum | 590 | 649 |
| mRaspberry | 598 | 625 |
| mNeptune | 600 | 650 |
| E2-Crimson | 611 | 646 |
| Monochlorobimane | 380 | 461 |
| Calcein | 496 | 517 |

In some applications, particularly clinical applications, it can be desirable to use microfluidics to introduce samples to the apparatus. The microfluidic device can be disposable (i.e., used once or perhaps a few times, followed by disposal and replacement) and/or composed of a polymeric material. The microfluidic device can be adapted to reduce the amount of sample used to determine whether a patient can benefit from a particular anti-thrombotic therapy. The microfluidic device preferably provides a tip adapted for delivering the biological sample including the platelets into the cell through which light passes, so that the platelets can then travel through the light beam(s). In some embodiments, the tip is adapted for sheath spraying. In other embodiments, the tip is adapted for non-sheath spraying. In any of the embodiments herein the apparatus may include a disposable inlet capillary.

The apparatus can also include an autodiluter, which can start with the most dilute sample, rather than the most concentrated sample, and can therefore use less sample. Autodiluters are well known to those of skill in the art. Representative autodiluters include the AutoDiluter-5.2, the CETAC ADX-500 Autodiluter, the ProLiquid AutoDiluter, and the DYNATECH Autodiluter III.

In high-throughput screening, it can be preferable to include robotics, which can introduce the samples to the apparatus. Ideally, the apparatus can then be cleaned in between samples, for example, by flushing the various lines, and subsequent samples introduced, enabling the screening to be automated. Information on the screening results can be stored, for example, in a memory map, and the information correlated with the patient's identity.

A "focused light scattering device" is a single-particle optical sensor, which has high sensitivity and responds to relatively concentrated suspensions, uses a relatively narrow light beam to illuminate an optical sensing zone non-uniformly. It differs from conventional SPOS devices in that it can handle more concentrated solutions and smaller particle sizes.

In use, a solution including suspended platelets passes through a zone. The zone is smaller than the flow channel, so that the sensor responds to only a fraction of the total number of platelets flowing through the channel, detecting a statistically significant number of particles of any relevant diameter.

Because different particle trajectories flow through different parts of the zone illuminated at different intensities, it is necessary to deconvolute the result. Two methods of deconvolution can be used: modified matrix inversion or successive subtraction. Both methods use a few basis vectors measured empirically or computed from a theoretical model, and the remaining basis vectors are derived from these few. The sensor is compensated for turbidity.

The sensor apparatus for single-particle optical sizing of particles in a fluid suspension typically includes a means for establishing flow of the suspension through a physically well-defined measurement flow channel. There is also an illumination means for effectively directing a relatively narrow beam of light, having an axis, through the measurement flow channel to form an optical sensing zone within the measurement flow channel. The beam of light and the optical sensing zone are of such size relative to the size of the measurement flow channel that the sensor apparatus responds to only a fraction of the total number of particles flowing through the measurement flow channel. In this manner, the sensor apparatus responds effectively to a relatively concentrated fluid suspension.

The beam has a maximum intensity portion and a continuum of lesser intensities for positions spaced transverse to the axis from the maximum intensity portion. In this manner, some of the particles have trajectories through the maximum intensity portion, others of the particles have trajectories through the lesser intensity positions, and still others of the particles may have trajectories outside the zone. Typically, the maximum intensity portion of the beam is in a central portion of the beam.

The device also includes a detector means for photo-detecting light from the zone to provide pulse height signals. These signals each respond to a particle flowing through the zone. The pulse height signals are functions of the sizes and trajectories of detected particles. Particles of a given size provide a maximum pulse height signal when flowing through the maximum intensity portion, and lesser pulse height signals when flowing through the lesser intensity positions of the zone. The pulse height signals, collectively, form a pulse height distribution PHD.

The device further includes a means for mathematically deconvoluting the pulse height distribution to extract a particle size distribution of the PSD particles in the fluid suspension. The sensor apparatus can detect a statistically significant number of particles of any given diameter or range of diameters that are relevant to the fluid suspension.

In one embodiment, the measurement flow channel has a thickness dimension axially of the beam of light, a width dimension transverse to the beam, and a flow direction substantially perpendicular to the thickness and width dimensions. The beam is narrower than the measurement flow channel in the width direction. The beam can be focused with a depth of field which is substantially larger than the thickness dimension, and the beam substantially has an effective width which does not vary substantially over the thickness dimension.

In another embodiment, the beam has an effective width between opposing positions transverse to the axis in the beam, at which the lesser intensities have fallen to a given fraction of the maximum intensity. The effective width is chosen so that the largest particles of interest can be effectively sized. The given fraction can be, for example, $1/e^2$ of the maximum intensity, where e is the base of the natural system of logarithms, and the effective width is substantially one half the size of the largest particle to be sized.

In yet another embodiment, the apparatus uses hydrodynamic sample injection, such as is described in Pelssers et al., Journal of Colloid and Interface Science, Volume 137, Issue 2, July 1990, Pages 350-361. Colloidal dispersions, such as platelets in serum or other media, can be hydrodynamically focused into a narrow stream, with widths ranging from about 3 to about 10, preferably about μm width. The use of a focused light scattering technique allows one to measure relatively small particle sizes. However, where a focused beam hits particles in a relatively wide sample stream (as described above, where the beam is narrower than the measurement flow channel in the width direction), the detection method relies somewhat on statistics. That is, where the beam is substantially narrower than the sample stream, an assumption is made that there is an equal distribution of particles in the sample stream, so that one can extrapolate the results of the interaction of the light in the narrow beam with the particles in its path over the entire width of the sample stream. By hydrodynamically focusing the sample into a stream with a relatively narrow width, and using a focused light source, it is possible to count all or most of the particles in the sample stream, and rely to a lesser extent on statistics.

The light beam can have, for example, a Gaussian intensity profile, a circular cross-section, or an elliptical cross-section being wider in a direction transverse to particle flow.

The detector means can be include a light extinction-type detector, and can be a combination of detectors, for example, a light-extinction detector type and a light-scattering type detector. The light-scattering type detector means can include means for passing a portion of scattered light from the zone through a mask to select light scattered between a first and a second angle to the beam and a means for directing a portion of the light transmitted through the zone to a light-extinction type detector.

The detector means can include a mirror for deflecting a portion of the light from the optical-sensing zone to the light-extinction detector. The illuminating means can include a light source and optical fiber means for conveying light from the light source to the optical sensing zone, and projecting the light through the zone.

The detector means can also include an optical fiber means for conveying the light passing through the optical sensing zone to the light-extinction type detector. The detector means can also include means for passing a portion of the light scattered from the zone through a mask, to select light scattered between a first and second angle to the beam, and an optical fiber means for conveying the portion of the light to a light-scattering type detector. The detector means can also include a light-scattering detector.

In one embodiment, the illumination means provides two light beams directed through a pair of optical sensing zones positioned within the measuring flow channel, and each beam has an effective width determined by a desired maximum particle size.

The detector means can include a light-scattering detector and a means for passing light scattered from the zone through a mask means. The mask means can include a plurality of masks and means for selecting one of the masks for passing the light scattered from the zone, each mask defining different angles between which the light is scattered. The masks can be located on a rotatable wheel, and a mask can be selected by rotating the wheel to a desired position.

The illuminating means can project a relatively wide collimated beam through the optical sensing zone, and can include an acceptance aperture to capture only those light rays that closely surround the axis of the beam. This reduces the effective width of the beam to a width in a direction transverse to the axis of the light beam which is substantially one-half the size of the largest particle to be sized. The illuminating means can also include a means for coupling the light rays to the detector means. This can be, for example, an optical fiber means.

In one aspect of the invention, a statistically significant number of particles of each relevant size flow through all portions and positions of the zone.

In another aspect of the invention, the fluid suspension is relatively concentrated and the apparatus further comprises means to compensate for turbidity of the suspension. In this aspect, the detector means can operate on a light extinction principle, and provide a signal having a baseline voltage level. The pulse height signals appear as downwardly extending pulses from the baseline voltage level, and the means for compensation for turbidity of the suspension can include means to sense the baseline voltage level and automatically increase the level to approximately the baseline voltage level present in the absence of turbidity in the suspension. The detector means can operate on a light extinction principle, and provide a signal having a baseline voltage level, wherein the means to compensate for turbidity can include a computer means for correcting the pulse height signals in response to the ratio of the baseline voltage level when the fluid suspension is not turbid, to the baseline voltage level for the turbid fluid suspension.

The detector means can also operate on a light extinction principle and provide a signal having a baseline voltage level, wherein the means to compensate for turbidity includes a means to adjust the intensity of the beam of light by increasing the amount of light produced by the illuminating means in response to the ratio of the baseline voltage level when the fluid suspension is not turbid, to the baseline voltage level for the turbid fluid suspension.

The particle trajectories can be substantially uniformly distributed across the width of the measurement flow channel.

The means for deconvoluting the pulse height distribution can include basis vectors, each corresponding to a particular particle size, and a source vector representing a measured pulse height distribution for a fluid suspension as detected by the detector means. There can also be a means using a deconvolution algorithm to derive the particle size distribution from the pulse height distribution. At least some of the basis vectors can have values based upon measurements of particles of known size. Some of the basis vectors can also have values based upon measurements of particles of known size and others of the basis vectors can be computed from the sum of the basis vectors by interpolation and/or extrapolation.

The basis vectors can be computed, and the basis vectors can be column basis vectors of a matrix, where the means using a deconvolution algorithm performs matrix inversion and vector multiplication, or the means using a deconvolution algorithm can perform successive subtraction.

The means using a deconvolution algorithm can provide a deconvoluted pulse height distribution dPHD, and the apparatus further comprises means providing a calibration curve of the relationship of pulse height and diameter, and means using the calibration curve to transform each deconvoluted pulse height value in the dPHD into a unique particle diameter associated with this pulse height value. This can yield a "raw" particle size distribution PSD. There can also be a means for converting the raw PSD into a final PSD by renormalizing the raw PSD by multiplying by the value $1/\mathrm{PHI}_d$, where $\mathrm{PHI}_d$ is the fraction of particles actually detected by the device for particles of each size.

The particle trajectories can be distributed non-uniformly across the width of the measurement flow channel, and the basis vectors can be based upon the response of particles of known size flowing through the measurement flow channel with the same non-uniform distribution of particle trajectories as the fluid suspension.

The sensor apparatus may respond only to a fraction of the total number of particles flowing through the measurement flow channel.

One can prepare a matrix for deconvoluting pulse height distributions derived from particles of unknown size flowing along different trajectories through a non-uniform light field of a single-particle optical sizing device. This can enable one to size particles in a fluid suspension. To do this, one can determine the value of at least one empirical basis vector for the matrix by measuring the response of particles of known size flowing through the single-particle optical sizing device. Then, one can compute other basis vectors for the matrix corresponding to particles of other sizes, by interpolating and/or extrapolating the other basis vectors from the empirical basis vector.

One can also determine the value of additional empirical basis vectors for the matrix by measuring the response of particles of known sizes flowing through the single-particle optical sizing device, and computing the other basis vectors for the matrix corresponding to particles of other sizes from the at least one empirical basis vector and the additional empirical basis vectors.

Another way to prepare a matrix for deconvoluting pulse height distributions derived from particles of unknown size flowing along different trajectories through a non-uniform light field of a single-particle optical sizing device for sizing particles in a fluid suspension involves determining the value of at least one computed basis vector corresponding to particles of at least one size for the matrix. One can compute other basis vectors for the matrix corresponding to particles of other sizes from computed basis vectors.

Also disclosed is a method of deconvoluting a pulse height distribution derived from particles of unknown size flowing along different trajectories through a non-uniform light field of a single-particle optical sizing device for sizing particles in a fluid suspension. The method involves setting up a matrix having a plurality of columns, each containing a basis vector comprising a pulse height distribution of particles of a known size corresponding to the response of a photo-detector of the device to the particles of known size. Each successive column contains a basis vector for particles of successively larger sizes. The matrix also has a like plurality of rows, each corresponding to a successive pulse height channel, each channel including a range of pulse heights, with successive rows corresponding to successively larger pulse heights, and with each column having a maximum count pulse height value at a location for a row which relates to a pulse height corresponding to the particle of known size associated with the column. The maximum count pulse height values for successive columns are arranged on a diagonal of the matrix. The matrix is modified by setting all terms corresponding to pulse height values greater than the maximum count pulse height value in a column to zero. A deconvolution algorithm is used to perform matrix inversion and vector multiplication of the pulse height distribution and the matrix as modified.

Before the modifying step, one can renormalize the values of the basis vectors in the columns by setting the maximum count pulse height value to equal 1.0 and all other count pulse height values in the column to a value maintaining the same proportionate value to 1.0 that the other count pulse height values had to the maximum count pulse height value of the column.

The response of the photo-detection to the particles of known size is developed empirically for some of the basis vectors by sending particles of the substantially known size through the device and providing a response by the device to the particles of known size. The response to the photo-detector for the remaining basis vectors can be computed by interpolating and/or extrapolating the response for the remaining basis vectors from the some of basis vectors.

The response of the photo-detector to the particles of known size can be computed for some of the basis vectors and the response to the photo-detector for the remaining basis vectors can be computed by interpolating and/or extrapolating the response from the some basis vectors.

A pulse height distribution ("PHD") can be derived from particles of unknown size flowing along different trajectories through a non-uniform light field of a single-particle optical sizing device for sizing particles in a fluid suspension can be deconvoluted by setting up a matrix having a plurality of columns. Each column includes a basis vector comprising a pulse height distribution of particles of a substantially known size corresponding to the response of a photo-detector of the device to the particles of known size, and each successive column contains a basis vector for particles of successively larger sizes. The matrix can also include a like plurality of rows, each corresponding to a successive pulse height channel, each channel including a range of pulse heights, successive rows corresponding to successively larger pulse heights, each column having a maximum count pulse height value at a location for a row which relates to a pulse height corresponding to the particle of known size associates with the column. The maximum count pulse height values for successive columns can be arranged on a diagonal of the matrix. A successive subtraction algorithm can be implemented, by starting with the basis vector with its maximum count value in the largest row number; scaling a column basis vector by a factor corresponding to the value of the row in the PHD that matches the column number; subtracting the scaled basis vector from the PHD to form an element of a deconvoluted PHD (dPHD), leaving an intermediate PHD vector with a smaller number of total particles; and repeating this process using the remaining basis vectors until the entire PHD has been consumed and all the elements of the deconvoluted dPHD have been formed.

A single-particle optical sizing sensor for sizing particles in a relatively concentrated fluid suspension sample for turbidity of the suspension sample can be compensated using a sensor operating on a light extinction principle whereby a photo-detector produces signal $V_{LE}(t)$ having a baseline voltage level and a response to blockage of light by a particle as a downwardly extending pulse from the baseline voltage level. The compensation method involves passing a non-turbid suspension through the sensor; measuring a baseline voltage level $V_0$ produced in response to the non-turbid suspension; passing the relatively concentrated suspension sample through the sensor; measuring a baseline voltage $V_0^T$ produced in response to the relatively concentrated suspension sample, calculating the ratio $V_o V_0^T$; and adjusting the sensor in response to G to compensate for the turbidity when the relatively concentrated suspension sample passes through the sensor.

The baseline voltage $V_0^T$ can effectively be subtracted from the signal $V_{LE}(t)$, the remaining signal can be inverted to produce a pulse height signal 2 $V_{LE}^T(t)$, and an adjustable gain amplifying means can be used to amplify the pulse height signal 3 $V_{LE}^T(t)$. The adjustable gain amplifying means can be controlled by the ratio G to provide a compensated pulse height signal $\Delta V_{LE(t)}$.

The signal $V_{LE}(t)$ produced by the sensor in response to the relatively concentrated suspension sample can be amplified by adjustable gain amplifier means, the gain of which is controlled by the ratio G to provide a compensated signal $V_{LE}(t)$ having a compensated baseline voltage $V_0$, subtracting the baseline voltage $V_0$ from the compensated signal $V_{LE}(t)$, and inverting the remaining signal to produce compensated pulse height signal $\Delta V_{LE}(t)$.

In one embodiment, the single-particle optical sizing sensor comprises a light source producing a light beam of adjustable intensity, wherein the intensity is increased in response to the ratio G to compensate for the turbidity.

Particles in a fluid suspension can also be optically sized by establishing a flow of the suspension through a physically well-defined measurement flow channel of a single-particle optical sizing sensor apparatus wherein a beam of light, having an axis, is directed through the measurement flow channel to form an optical sensing zone within the measurement flow channel. The beam of light and the optical sensing zone are ideally of such size relative to the size of the measurement flow channel that the sensor apparatus responds to only a fraction of the total number of particles flowing through the measurement flow channel. The sensor apparatus can respond effectively to a relatively concentrated fluid suspension. The beam can have a maximum intensity portion in the beam and a continuum of lesser intensities for positions in the beam spaced transversely from the axis, whereby some of the particles have a trajectory through the maximum intensity portion, others of the particles have trajectories through the lesser intensity positions, and still others of the particles may have trajectories outside the zone. Light from the zone can be detected to provide pulse height signals, each responsive to a particle flowing through the zone. The pulse height signals are functions of the sizes and trajectories of detected particles, and the pulse height signals collectively form a pulse height distribution PHD. The PDH can be mathematically deconvoluted and processed to extract from the PHD a particle size distribution PSD of the particles in the fluid suspension.

The step of mathematically deconvoluting the PHD can involve determining the value of at least one empirical basis vector by measuring the response to particles of known size flowing through the single-particle optical sizing device. Other basis vectors corresponding to particles of other sizes can be computed by interpolating and/or extrapolating the other basis vectors from the empirical basis vector.

The value of additional empirical basis vectors for particles of known sizes flowing through the single-particle optical sizing device can be determined; and the other basis vectors for the matrix corresponding to particles of other sizes can be calculated by interpolating and/or extrapolating the other basis vectors from at least one empirical basis vector and the additional empirical basis vectors. The method can further involve determining the value of at least one computed basis vector corresponding to particles of at least one size. Other basis vectors corresponding to particles of other sizes can also be computed by interpolating and/or extrapolating the other basis vectors from computed basis vectors.

The step of deconvoluting and processing the PHD can involve setting up a matrix having a plurality of columns, each containing a basis vector comprising a pulse height distribution of particles of a known size corresponding to the response of a photo-detector of the device to the particles of known size, each successive column containing a basis vector for particles of successively larger sizes. The matrix can also have a like plurality of rows, each corresponding to a successive pulse height channel, each channel including a range of pulse heights, successive rows corresponding to successively larger pulse heights, each column having a maximum count pulse height value at a location for a row which relates to pulse heights corresponding to the particle of known size associated with the column. The maximum count pulse height values for successive columns can be arranged on a diagonal of the matrix. The matrix can be modified by setting all terms corresponding to pulse height values greater than the maximum count pulse height value in a column to zero. A deconvolution algorithm can be used to perform matrix inversion and vector multiplication of the pulse height distribution and the inverted matrix as modified. The response of the photo-detector to the particles of known size can be developed empirically for some of the basis vectors by directing a flow of particles of the known size through the device and providing a response by the device to the particles of known size. The response to the photo-detector for the remaining basis vectors can be calculated by interpolating and/or extrapolating the response for the remaining basis vectors from the some of basis vectors.

The step of mathematically deconvoluting the PHD can also involve using a deconvolution algorithm to provide a deconvoluted pulse height distribution dPHD. The method can further involve providing a calibration curve of the relationship of pulse height and diameter, and using the calibration curve to translate each deconvoluted pulse height value in the dPHD into a unique particle diameter associated with this pulse height value yielding a "raw" particle size distribution in PSD. The raw PSD can be converted into a final PSD by renormalizing the raw PSD by multiplying by the value $1/\mathrm{PHI}_d$, where $\mathrm{PHI}_d$ is the fraction of particles actually detected by the device for particles of each size.

In use, a focused laser light beam passes through a chamber through which fluid flows, and the laser light scatters as the particles pass through the focused laser beam. An extinction detector determines when particles have passed through the beam. In the absence of a particle interfering with the beam of light, the light would pass, uninterrupted, to the extinction detector. When a particle blocks the passage of light, the resulting loss of light hitting the extinction detector signals that a particle has passed through the beam. The light hitting the particles is reflected, and passed through a scatter colli-mating lens, which re-focuses the light, which then passes through a scatter focus lens, which sends a single beam through to a scatter detector.

A representative focused light scattering device is shown in FIG. 1. A first laser (1) emits light at a first wavelength, and a second laser (2) emits light at a second wavelength. Both beams of light pass through a first beam splitter (3) and through a first focusing lens (4) before they enter into a flow cell (15). The flow cell includes a site (5) for hydrodynamic injection of the sample. As the platelets in the flow cell pass through the beams of light, the light is scattered as it hits the platelets. The scattered light passes through a circular spatial filter (6) and then through a first collimating lens (7). The light beam passes through a second beam splitter (16), which splits the light into two beams. A first beam passes through a second focusing lens (8) and through a first chromatic filter (9) that passes scattered light from the first laser (1) through a first detector (10). The second beam passes through a second collimating lens (11), a third focusing lens (12) and a second chromatic filter (13) that passes scattered light from the second laser (2) to a second detector (14).

The two photodetectors (10 and 14) each are able to detect light at a certain frequency, so that light transmitted at different frequencies (as a result of the two lasers hitting particles, and which may interact with fluorescent tags on the particles) can be separately determined.

A third detector (an extinction detector) (18) receives a portion of the light passing through the flow cell. A portion of the light passing through the flow cell is reflected off of a movable mirror (17) and onto the third detector.

Figure 2:
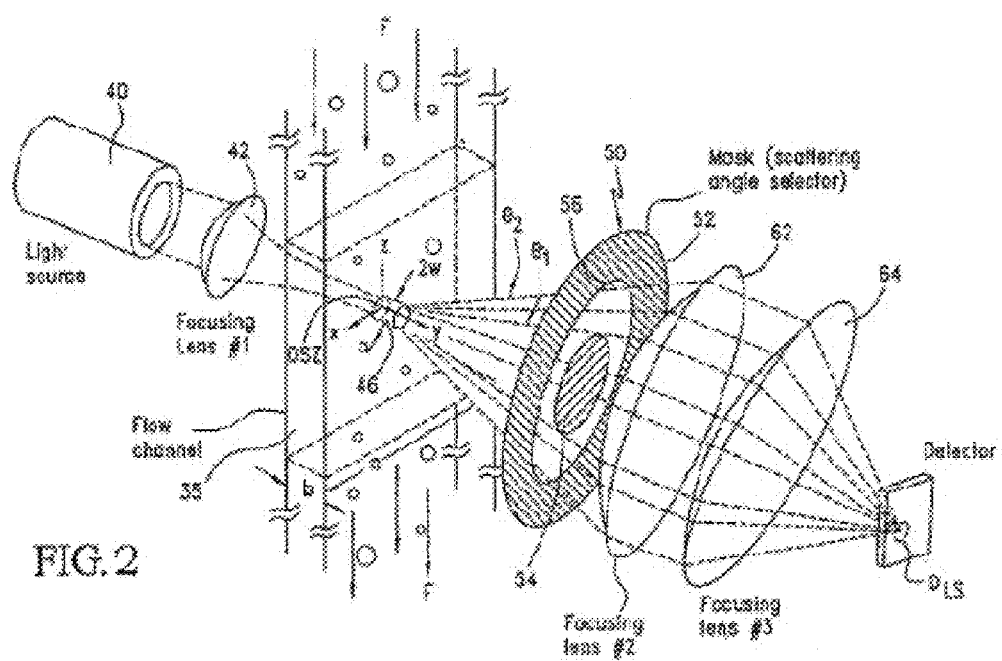
FIG. 2 is a schematic illustration of a device used for focused light scattering, using a single light source and a single detector.

As is shown in FIG. 2, there are two important features inherent in the optical design. First, the incident beam alone (in conjunction with the front and back windows 36 and 37 of the measurement flow channel 35) defines the OSZ. The side walls 38 and 39 that confine the fluid-particle suspension along the x-axis are no longer of any consequence with respect to definition of the OSZ. Second, the physical volume associated with the OSZ can no longer be described by a single value; rather, it now depends on the size of the particles being measured.

The approach shown schematically in FIG. 2 involves illuminating measurement flow channel 35 with a light beam 41 from a laser light source 40 which is focused by a lens 42 to form a beam 44 of relatively narrow cross section—i.e., smaller than. a typical illuminated width, a, of the flow cell in a conventional LE-type sensor. The resulting OSZ is therefore defined approximately by a "pencil" beam of light 46, together with the front and back windows of the flow cell, separated by dimension "b." The schematic diagram in FIG. 2 provides a simplified picture of the OSZ defined by focused light beam 46. First, the region of illumination that comprises the OSZ is not sharply defined, as implied by the approximately cylindrical zone indicated in FIG. 1. Rather, the outer boundary of the OSZ is "fuzzy," extending well beyond the zone indicated, as discussed below. Second, the beam passing through the flow channel 10, assuming that it has been focused, typically is not uniform in width. Rather, in the case of a focused beam, its width varies over the depth of the measurement flow cell 35. The extent to which the beam waist varies over the depth of the channel depends on the depth of field of the focused beam, defined as the distance (y-axis) between the points at which the beam waist grows to 2 times its minimum value. Ideally, the depth of field is significantly greater than the channel thickness, b, resulting in a relatively uniform beam width throughout the flow channel.

Consequently, focused light scattering devices may include a fundamentally different sensor. In the conventional design, the physical width of the flow channel 10 and the effective width (x-axis) of the OSZ are one and the same, equal to dimension "a." By contrast, the physical width of the flow channel in a sensor used for focused light scattering devices (also defined as "a") is typically much larger than the nominal width, 2w, of the incident light beam and therefore has no significant influence on the OSZ. Hence, the spacers (or shims) 38 and 39 that separate the front and back windows 36 and 37, determining the depth, b, of the flow cell (and OSZ), no longer need to be opaque or smooth on an optical scale to avoid scattering by the edges. This is a significant advantage, making fabrication of the flow cell easier and less expensive.

It is usually convenient and effective to employ a "circularized" light beam, in which the incident intensity ideally depends only on the radial distance, r, from the beam axis (coincident with the y-axis, with $x=z=0$, as seen in FIG. 1). Typically, one employs a "Gaussian" light beam—i.e. one having a Gaussian intensity profile, described in the focal plane (minimum beam waist), at $y=b/2$, by $I(r)=I_0 \exp(-2r^2/w^2)$ (7) where $r^2=x^2+z^2$ for the assumed circular beam.

Quantity 2w is the diameter of an imaginary cylinder containing most of the incident light flux. The intensity on its surface equals $1/e^2$, where e is the base for natural logarithms, or 0.135 times its value, $I^0$, at the center of the beam ($r=0$). Essentially 100% (apart from losses due to reflections at optical interfaces and extinction by particles in the beam) of the light flux contained in the incident beam traverses the fluid-particle mixture in the flow channel and impinges on the distant detector $D_{LE}$. This causes detector $D_{LE}$ to provide a light extinction signal $V_{LE}$ in the form of a downwardly extending pulse.

This behavior is in sharp contrast to the illumination scheme employed in a conventional LE-type sensor. There, the starting light beam is expanded greatly along the lateral (x) axis of the flow cell, so that its width ($1/e^2$ intensity) is much larger than the width, a, of the front window (and OSZ). As a result, there is relatively little variation in the incident intensity along the x-axis (i.e. for $y=z=0$) where the beam enters the flow cell, because the light is captured at the top of the x-expanded Gaussian beam. Therefore, a particle passing through the OSZ will experience substantially the same maximum beam intensity (i.e. at $z=0$), regardless of its trajectory. The specific values of x and y defining the trajectory ideally have no influence on the resulting sensor response, i.e. the pulse height.

There is a sharp contrast between the conventional optical design and the scheme employed in the sensor used for focused light scattering devices. There is a large variation in the incident intensity as a function of position (x-axis) across the width of the flow channel. In the case in which the incident light beam has a symmetric (circular) Gaussian profile, the intensity variation is given by Equation 7, with $r=x$. The maximum intensity, $I_0$, is achieved at the center of the beam ($x=0$), where for simplicity $x=0$ represents the midpoint of the channel (with the side walls at $x=\pm a/2$). As noted, the intensity occurring at $x=\pm w$, $z=0$ is reduced substantially, to 0.135 $I_0$. The intensity drops steeply with increasing distance from the beam, falling, for example, to 0.018 $I_0$ at $x=\pm 2w$, $z=0$ and 0.00033 $I_0$ at $x=\pm 4$ w, $z=0$.

The consequences for the light-extinction signal thus generated by the passage of particles through the new OSZ are far-reaching. First, as for a conventional LE-type sensor, the pulse height, $\Delta V_{LE}$, generated by passage of a particle through the OSZ in general increases with increasing particle size, all other factors being equal. In general, the larger the particle, the larger the fraction of light "removed" from the incident beam, thus unable to reach the detector $D_{LE}$. However, with the new sensor the fraction of light removed from the beam now depends on the precise trajectory of the particle—specifically, the minimum distance, $|x|$, of the particle to the center of the beam, $x=0$. (To first approximation, the response of the sensor will not vary significantly with changes in the y-axis value of the trajectory, assuming that the beam width is approximately constant over the depth of the flow channel, given an appropriately large depth of field, as discussed above.)

For a particle of given size and composition (hereinafter assumed to be spherical and homogeneous, for simplicity), the maximum "signal," or pulse height, is achieved when the particle passes through the center of the beam, $x=0$. A particle of given effective cross-sectional area, $\Delta A$, blocks the largest amount of incident light at the center of the beam, where the intensity is greatest. Particles of identical size that pass through the flow channel along different trajectories, with different minimum distances, $|x|$, from the beam axis, are exposed to varying, but smaller, maximum levels of illumination. The greater the distance from the beam axis, the lower the integrated intensity incident on a particle and, hence, the less light flux removed from the beam, and the smaller the resulting pulse height. The response therefore consists of a continuous "spectrum" of pulse heights, ranging from a maximum value, for trajectories that pass through the center of the beam, to essentially zero (i.e. indistinguishable from noise fluctuations), for trajectories located very far from the incident beam ($|x|>>w$). The maximum pulse height depends on the beam waist, 2w, and the size of the particles, as well as in some cases the refractive indices of the particles and surrounding fluid. (This depends on the extent to which light scattering is significant relative to refraction and reflection in contributing to the overall light extinction signal.) A crucial assumption is that the particle trajectories are distributed randomly (i.e. occur with equal frequency) within the flow channel. This assumption is usually valid, given the typical dimensions of the flow channel and the relatively low flow rates utilized. It is also assumed that the number of particles passing through the sensor is sufficiently large that the statistical fluctuations in the number of particles having trajectories with any given x-axis value (i.e. over any (narrow) range of x values) can be ignored.

The relationship between particle size and pulse height for the sensor in a focused light scattering device is therefore radically different from that obtained for a sensor of conventional design. In the latter case, irrespective of their trajectories, particles of a given size (and composition) give rise to pulses of nearly uniform height. This behavior is important for sensor design for the conventional SPOS method. The typically small variations in pulse height that occur, for example, when measuring polystyrene latex "standard" particles of essentially uniform size are caused by variations in the incident beam intensity within the OSZ along the x- and y-axes, for a given z-axis value. These variations ultimately determine the resolution of the sensor. The resulting width of the PSD is therefore mostly a consequence of residual non-uniformity of illumination across the OSZ, rather than an actual range of particle diameters.

By contrast, there is an obvious deterioration in the particle size resolution for sensor design for focused light scattering devices. When a single particle passes through the sensor, it gives rise to a light-extinction pulse with a height, $\Delta V_{LE}$ that can vary between a given maximum value and essentially zero. Conversely, given a single detected pulse, it is impossible to determine the size of the particle that has produced it, solely from knowledge of the pulse height. For example, a particle that is relatively small, but which passes directly through the beam axis, yields the maximum pulse height possible for a particle of that size (and composition). Alternatively, a particle that is much larger but which passes relatively far from the beam axis yields a pulse height that could actually be the same, depending on its size and trajectory. Even though the large particle is able to intercept a much larger area of incident illumination than the small one, the average intensity incident on it is smaller than the intensity incident on the small particle. Hence, the resulting pulse height could turn out to be the same as that produced by the small particle. Obviously, there are an infinite number of pairs, {d, |x|}, of particle diameters and minimum beam-trajectory distances that can give rise to the same pulse height. The particle diameter, d, and the resulting pulse height, $\Delta V_{LE}$, are effectively "decoupled" from each other. This is the problem of "trajectory ambiguity", which for more than twenty years has motivated the search for new light-scattering based schemes for particle size determination using Gaussian beams.

The effects of trajectory ambiguity described above might present a difficulty in measuring the size of a single particle, or a relatively small number of particles. However, the apparently poor size resolution associated with the sensor used for focused light scattering devices can be restored to a very acceptable level by means of appropriate mathematical deconvolution of the pulse-height data. The resulting dramatic improvement in the effective sensor resolution is possible by virtue of the fact that the sensor in a focused light scattering device is intended to be exposed to a large, statistically significant number of particles of every relevant diameter, or range of diameters, contained in the sample of interest. This is the circumstance that renders the new sensing method very useful for particle size analysis, in sharp contrast to the situation that holds for "contamination" applications. There, the sensor is exposed to relatively small numbers of particles of any given size, for which statistical significance is often not achieved.

The "raw" response of the sensor used in a focused-beam device, like its conventional SPOS predecessor, consists of the pulse height distribution (PHD)—a histogram of particle "counts" vs pulse height, $\Delta V_3$. The pulse-height scale is typically divided into a relatively large number (e.g. 32, 64 or 128) of "channels," or "bins," each of which encompasses an appropriately narrow range of pulse height voltages, thus defining the voltage resolution of the PH). It is usually convenient to establish channels that are evenly spaced on a logarithmic voltage scale. Measurement of a new pulse causes the number of particle counts stored in the appropriate pulse height channel in the histogram to be incremented by one. Data are ideally collected from the particle suspension of interest for a sufficiently long time that the resulting PHD becomes statistically reliable, and thus smooth and reproducible. This means that the number, $N_I$, of particle counts collected in the I-th pulse-height channel is statistically significant, dominating the fluctuations due to statistical "noise," for all I, e.g. for $1 \leq I \leq 128$, in the case of 128 channels. Assuming Poisson statistics, this means that $N_I \gg N_I$, for all I.

Relatively high levels of particle concentration are possible because the sensor responds to only a small fraction of the total number of particles passing through it. For example, concentrations in the range of hundreds of thousands of particles/ml, in sample sizes of tens of mls, can be measured. That is, millions of particles can be present, a portion of which is passed through the beam of light and counted. The fraction of particles that are actually counted, relative to the number of particles present in the sample (Np), is known as phi$_d$, or "sensor efficiency," and is calculated by taking the ratio of the particles actually detected over the number of particles in the sample. The number of particles detected over the number of particles in the sample typically ranges from about 0.5 to about 5%.

The fact that the sensor efficiency is so relatively small is not surprising. In the case of a tightly focused beam, the width, a, of the flow channel is invariably much larger than the nominal width, 2w, of the focused beam. Therefore, most of the particles passing through the sensor are exposed to negligible levels of light intensity, because their trajectories are located so relatively far from the beam axis—i.e. $|x| \gg w$. Consequently, only a small fraction of the total number of particles is able to "block" enough light to give rise to detectable pulses, relative to the prevailing noise level. The great majority of particles pass undetected through the sensor.

While this limitation may appear to be serious, in practice it is of little concern, for two reasons. First, the fraction, phi$_d$, of particles that produce detectable, measurable pulses will be fixed for a given sensor width, a, even though the value changes with particle diameter, d. Second, the new sensing method is intended for use in determining the particle size distribution (PSD) for samples that, by definition, are highly concentrated to begin with. Even following dilution, if required, the concentration of particles of any given size (i.e. within any (narrow) size range) is, by definition, relatively high. Assuming a suitable flow rate and data collection time, the resulting PHD will possess an acceptable signal/noise ratio, with a low level of statistical fluctuations. Hence, even though only a small fraction of the available particles will contribute to the raw data, the resulting PHD will be representative of the much larger number of particles in the sample that are ignored. Therefore, a reliable and accurate PSD, representative of the entire sample, can be obtained from the "inefficient" sensor used in the focused light scattering devices described herein.

Several additional features of the PHD that can be obtained are noteworthy. First, as a consequence of the fact that the particle trajectories span a large range of |x| values, passage of uniform particles through the sensor indeed results in a PHD containing a wide range of pulse heights. In this case, these range from the threshold of individual pulse detection (dictated by the prevailing r.m.s. noise level), roughly 5 millivolts (mV), to a maximum of approximately 326 mV for the nominal "end" of the distribution. (This excludes a small number of "outlier" pulses, due to agglomerates and over-size primaries that extend to 500 mV). Given the uniformity of the particles, this 65-fold range of pulse heights can only be ascribed to differences in particle trajectory. (To a first approximation, one can neglect variations in the beam width over the depth of the flow channel, as discussed earlier.)

Second, as expected, the PHD is highly asymmetric, skewed greatly in the direction of smaller pulse heights. Clearly, there are many particle trajectories that sample a large range of |x| values (and, hence, beam intensities), but only relatively few that probe the central portion of the Gaussian profile, where the intensity is substantially uniform. The PHD exhibits a broad, smooth upswing in the number of particles with increasing pulse height, accelerating to a relatively sharp peak, followed by a dramatic decline to the baseline, representing zero pulse events. This sharp "cut-off" at the upper end of the distribution defines the maximum pulse height, referred to hereafter as $^M\Delta V_{LE}$. The counts collected at this maximum value represent particles that passed through, or very close to, the center of the beam—i.e. trajectories with x approximately equal to 0—where the fraction of total incident light flux "blocked" by the particles is the largest value possible. The counts collected in smaller pulse height channels represent particles that passed further from the beam axis; the greater parameter |x|, the smaller the resulting pulse heights.

There is a relationship between the particle trajectory and the resulting pulse height. Trajectory "A" gives rise to extinction pulses having the maximum pulse height, $^M\Delta V_{LE}$, immediately preceding the upper cut-off of the PHD. Trajectories "B," "C," "D" and "E" located progressively further from the beam axis, give rise to pulses with correspondingly lower pulse heights and progressively lower numbers of particle counts. Eventually, the number of particle counts per channel approaches zero, as the pulse height reaches the detection limit (approximately equal to 5 mV).

The reproducibility of the PHD depends only on the degree to which the number of counts contained in the various channels is large compared to statistical fluctuations. Therefore, the "reliability" (i.e. the smoothness and reproducibility) of the PHD should depend on the total number of particles counted during a measurement. For a given particle size there will obviously exist a minimum number of pulses that should be counted and analyzed, below which the PHD should be expected to exhibit significant, irreproducible "structure" from one measurement to the next, due to statistical noise. Again, the PHDs produced by the new sensor have meaning only to the extent that relatively large, statistically meaningful numbers of particles of the same size are detected during the data collection period. Only if this is true can one expect to obtain optimal, reproducible PHD results, and correspondingly accurate, representative particle size distribution (PSD) results derived from the latter using the methods discussed below.

To confirm that the data measured is significant, one can overlay two or more PHDs taken from measuring the same sample in multiple runs.

Exposing the sensor to larger particles will yield a PHD that is shifted to larger pulse heights. Specifically, the maximum pulse height, $^M\Delta V_{LE}$, corresponding to particle trajectories passing through, or very close to, the beam axis, increases.

An LS-type sensor can be used in place of, or in addition to, an LE sensor. The LS-type sensor uses a light collection means—typically one or more lenses—in order to gather scattered light rays originating from individual particles passing through the OSZ, created by the incident light beam.

The lens system is designed to collect scattered light over a particular, optimal range of angles, typically encompassing relatively small angles of scattering. In the scheme shown in FIG. 2, a mask 50 has been placed in front of the first collection lens. Mask 50 comprises an outer opaque ring 52 and an inner opaque area 54, which form a transparent ring 56. Mask 50 allows only light rays with scattering angles, theta, located within an imaginary annular cone defined by angles $theta_1$ and $theta_2$ (i.e. $theta_1 \leq theta_2$) to impinge on the first collection lens 62. Typically, this lens is centered on the axis of the incident beam, at an appropriate distance (i.e. its focal length) from the center of the flow channel, causing a portion of the diverging scattered light rays from the OSZ to be captured by the lens and become approximately collimated. A second lens 64 can then be used to focus the resulting parallel scattered rays onto a suitable (small-area) detector DLs. The resulting signal is "conditioned" by one or more electronic circuits, typically including the functions of current-to-voltage conversion and amplification.

There is a crucial difference between the signal, $V_{LS}$, created by this optical scheme and the signal, $V_{LE}$, produced by the LE-type sensor. Unlike the latter, the LS-type sensor, by design, prevents the incident light beam emerging from the back window of the flow cell from reaching the detector, $D_{LS}$. Instead, the incident beam is either "trapped" by means of a suitable small opaque beam "stop" (e.g., the inner opaque area 54) or deflected by a small mirror away from the lens that is used to collect the scattered light rays originating from the OSZ. Consequently, the relatively large "baseline" level, V.sub.0, necessarily present in the overall signal, $V_{LE}$, produced by the LE-type sensor is now absent from the LS signal, $V_{LS}$. Ideally, the new "baseline" signal level is zero—i.e. there should be no scattered light generated from sources within the OSZ in the absence of a particle. In practice, of course, there will be some amount of background light caused by light scattered from the surfaces of the front and/or back windows of the flow channel, due to imperfections on, or contaminants attached to, the latter surfaces. In addition, there may be fluctuating background light due to scattering from small contaminant particles suspended in the diluent fluid. Also, for some samples there may be fluctuations in background light produced by a "sea" of ultra-fine particles which comprise a major fraction of the overall particle population, but which are too small to be detected individually.

When a particle of sufficient size passes through the OSZ, defined by the incident Gaussian light beam and front and back windows of flow channel 35, a momentary pulse occurs in the output signal produced by the detector, $D_{LS}$, and associated signal-conditioning circuit. In general, one might naively expect that the larger the particle, the greater the amount of light scattered by it, assuming the same trajectory, and therefore the greater the height of the signal pulse.

In practice, the actual pulse height depends not only on the size of the particle, but also its composition—specifically, its index of refraction (and that of the surrounding fluid) and absorbance, if any, at the incident wavelength. The pulse height also depends on the wavelength of the beam and the orientation of the particle as it passes through the OSZ, if it is not spherical and homogeneous. Finally, for particles comparable in size to, or larger than, the wavelength, the scattering intensity varies significantly with the scattering angle. Consequently, in this case the pulse height depends on the range of angles over which the scattered light is collected and measured.

The relationship between the scattered light "radiation pattern" (i.e. intensity vs angle) and all of these variables is described by classical Mie scattering theory, which takes into account the mutual interference of the scattered light waves within the particle. In general, the larger the particle, the more complex (i.e. non-isotropic) the angular dependence of the scattered intensity resulting from intra-particle interference. In order to optimize the response and performance of the LS-type sensor, one must confine the collection of scattered light to a range of angles, theta, for which the net integrated response, $\Delta V_{LE}$, increases monotonically with the diameter, d, of particles of a given composition (i.e. refractive index) over the largest possible, or expected, size range. This requirement can usually be satisfied by choosing a range of relatively small angles, $theta_1 < theta < theta_2$, close to the forward direction. In this way, one avoids "reversals" in the integrated scattering intensity with increasing particle size due to variations of the intensity with changes in angle, especially significant at larger angles as a consequence of Mie intra-particle interference.

There are two properties of the signal, $V_{LS}$, produced by the new LS-type sensor that are qualitatively different from the properties of the signal, $V_{LE}$, produced by the corresponding LE-type sensor. First, the signal pulse caused by passage of a particle through the OSZ and the "overall" signal, $V_{LS}$, are essentially the same in the case of the LS-type sensor. The relatively high background signal level that accompanies the pulse of interest in the LE-type sensor is absent: (The same situation clearly holds for a conventional LS-type sensor).

Therefore, in the case of relatively small particles that give rise to pulses of low magnitude, the signal/noise ratio achieved in practice using the LS method should be significantly better than that realized using the LE method. This advantage becomes more important the smaller the particle and the weaker the resulting pulse, as the latter approaches the prevailing noise fluctuations. Another way of appreciating the inherent advantage of the LS method over its LE counterpart is to realize that the former is based on "detection at null." That is, quantitative detection of a pulse ideally is carried out in the presence of zero background signal. From a signal/noise perspective, this is in sharp contrast to the situation that obtains for the LE method, which requires high "common-mode rejection." The "common-mode" signal, $V_0$, is always present in the raw signal, $V_{LE}$, and must be subtracted, or otherwise suppressed, in order to extract the (often small) signal pulse of interest.

There is a second important and distinguishing property of the LS signal, $V_{LS}$. The signal/noise ratio associated with the measurement of $\Delta V_{LS}$ can in principle be improved by increasing the power of the incident light beam, so as to increase the light intensity incident on a particle at all points within the OSZ. Therefore, in principle one can reduce the lower size detection limit for the new LS sensor by increasing the power of the light source, as for a conventional LS sensor. Eventually, a lowest size limit will be reached, based on noise fluctuations associated with the suspending fluid and/or the light source and detection system. Of course, as discussed above, the lower particle size limit can also be improved for the new LS-type sensor by reducing the width, 2w, of the incident beam, assuming no change in the power of the latter. This action will obviously increase the maximum intensity incident on the particles that pass through the beam axis (x=0), and therefore the height of the largest resulting pulse for a particle of given size, as well. However, this method of improving the sensitivity eventually reaches a point of diminishing return, due to limitations imposed by diffraction theory (establishing a minimum beam width) and excessive variation of the focused beam width over the depth, b, of the flow cell due to excessively-long depth of field.

By contrast, an increase in the power of the light source has relatively little effect on the lowest particle size that can be measured using the LE method. For example, a doubling of the power of the light source will result in a doubling of the baseline signal level (FIG. 2), to $2V_0$. The height of the pulse, $\Delta V_{LE}$, produced by a particle of the same size and trajectory will also be doubled, assuming no change in the beam width. However, the root-mean-square magnitude of the noise fluctuations associated with the relatively high baseline signal level will typically also be approximately doubled, because these fluctuations are usually associated with the light source and therefore scale with the output power. Hence, one expects little or no improvement in the signal/noise level for the LE-type sensor. Consequently, there should be little or no reduction in the lower size detection limit achievable by the LE method as a consequence of increasing the power of the light source. An improvement will be realized only if the signal/noise ratio associated with the light source improves with increased power.

When uniform size particles flow through the new LS-type sensor, depending on their trajectories they are individually exposed to different values of maximum incident intensity, given by Equation 7, with r=x, z=0. (For simplicity, it can be assumed that the particles are much smaller than the beam width, so that every point in a given particle is exposed to the same intensity at any given time.) Therefore, as with the new LE-type sensor, the height, $\Delta V_{LS}$, of the resulting pulse generated by a particle of given size depends on the distance, |x|, of closest approach (z=0) to the axis of the incident beam. The smaller the distance |x|, the larger the value of $\Delta V_{LS}$. Hence, like its LE counterpart, the LS-type sensor generates a distribution of widely varying pulse heights, $\Delta V_{LS}$, when a suspension of uniform particles passes through it at an appropriate flow rate. The shape of the resulting PHD bears a strong qualitative resemblance to the highly asymmetric shape of the PHDs obtained using the new LE method, exemplified in FIGS. 4, 6 and 7. That is, the number of pulse counts (y-axis) is relatively small at the smallest measurable pulse height just above the noise fluctuations) and rises with increasing pulse height, $\Delta V_{LS}$. The pulse count value culminates in a peak value at a maximum pulse height, referred to as $^M\Delta V_{LS}$, corresponding to particle trajectories for which |x|.apprxeq.0. Above $\Delta AV_{LS}$ the number of pulse counts ideally falls to zero, assuming that the particle concentration is below the coincidence concentration (discussed earlier) for particles of that size, so that at most one particle effectively occupies the OSZ at any given time. Of course, a PHD obtained using the new LS method usually pertains to particles that are smaller—often significantly so—than those used to generate a typical PHD using the new LE method.

As noted above, the shape of the PHD—number of pulse counts vs $\Delta V_{LS}$—generated for uniform particles using the new LS method is qualitatively similar to the shape of the PHD obtained for uniform (typically larger) particles using the new LE method. Both kinds of PHDs share the distinguishing characteristic of a sharp "cut-off" following their respective peak number of pulse counts, coinciding with their maximum pulse height values, $^M\Delta V_{LS}$ and $^M\Delta V_{LE}$. However, it should be appreciated that there are quantitative differences in the shapes of the two kinds of d=1, notwithstanding their qualitative similarities, even for the same particle size—e.g. d=1 µm. The "front end" design of the new LS-type sensor—i.e. the focused light beam and relatively thin flow cell—is essentially the same as that utilized for the new LE-type sensor. Therefore, what distinguishes one type of sensor from the other concerns the means and manner of light detection and the type and magnitude of the response pulses generated by each method, even in the case of particles of the same size. For the new LS method, the response is due only to light scattering, and its magnitude, $\Delta V_{LS}$, is proportional to the intensity of the light incident on the particle, all other relevant variables being the same.

By contrast, for the new LE method the magnitude of the response, $\Delta V_{LE}$, is a more complex function of the intensity incident on the particle. First, the response is due to a combination of physical effects—refraction (and reflection) plus light scattering. However, the scattering phenomenon asserts itself in an "inverse" sense. That is, a small fraction of the incident light flux is removed from the beam before it reaches the detector. Second, over the typical size range for which the new LE method is applicable, there is a substantial variation in the incident intensity across the particle. Therefore, it should not be surprising that the fractional change of pulse height due to a given change in |x|, dependent on both particle size and trajectory, is generally different for the two methods. Similarly, the fractional change in pulse height with particle diameter, dependent on both particle size and trajectory, is also generally different for the two methods.

The task of converting the "raw" data—the PHD—obtained from a sample of suspended particles into the object ultimately desired—the particle size distribution, or PSD, is described in detail below.

It is useful to compare this task conceptually with the operation required in the case of a conventional LE- or LS-type sensor. There, the height of the pulse due to passage of a particle through the OSZ is nearly independent of its trajectory, because the intensity of the incident beam is designed to be approximately constant across the flow channel (i.e. along the x-axis) for a given z-axis value (e.g. z=0). Consequently, particles of a given size ideally give rise to pulses of substantially the same height, and the resulting PHD is therefore, in effect, equivalent to the final desired PSD. There is a one-to-one correspondence between a given, measured pulse height, $\Delta V_{LE}$ (or $\Delta V_{LS}$), and the particle diameter, d. If particles of a larger or smaller size pass through the sensor, the resulting pulse heights are larger or smaller, respectively. A "calibration curve," consisting of pulse height vs particle diameter, is all that is needed to obtain, by simple interpolation, the PSD from the PHD. Obtaining the raw PHD data using the conventional SPOS method is equivalent to determining the final, desired PSD.

By contrast, as discussed earlier, the response of the LE- (or LS-) type sensor is much more "convoluted." Even in the simplest case of particles of a single size, the resulting PHD consists of a broad spectrum of pulse heights, from the smallest values just above the prevailing noise fluctuations, to the maximum value, $^M\Delta V_{LE}$ (or $^M\Delta V_{LS}$), associated with that size. Therefore, in the typical case of particles of widely varying size, the resulting PHD consists of an even wider assortment of pulse heights. No longer is there a simple correspondence between pulse height and particle size. It is therefore no longer a simple, straightforward procedure to transform the set of particle counts vs pulse-height values contained in the PHD into the desired size distribution—particle counts vs particle diameter.

It typically involves three procedures to convert the PHD to the desired PSD. First, the raw PHD must be inverted, or deconvoluted, using a specialized mathematical algorithm. Its purpose is to convert the "wide-spectrum" PHD produced by the new LE- (or LS-) type sensor into a "sharp", idealized PHD, equivalent, in effect, to what would have been obtained using a conventional LE- (or LS-) type sensor. Such an idealized, deconvoluted PHD—hereinafter referred to as the dPHD—has the property that all pulses of a given height, $\Delta V_{LE}$ (or $\Delta V_{LS}$), belong exclusively to particles of a given size (assuming, always, particles of a given composition). The dPHD is equivalent to what would have been obtained if all of the particles contributing to the original PHD had passed through the center (axis) of the incident beam.

A second straightforward procedure is then carried out. A preliminary, or "raw", PSD is obtained from the dPHD by simple interpolation of the calibration curve that applies to the specific new LE- (or LS-) type sensor utilized—e.g. the curve shown in FIG. 8A. This procedure permits a one-to-one translation of each deconvoluted pulse height value in the dPHD into a unique particle diameter associated with this value, thus yielding the raw PSD. A third procedure is then needed to convert the raw PSD thus obtained into a final PSD that is quantitatively accurate. The number of particle counts in each diameter channel of the raw PSD is the number of this size that actually contributed to the measured PHD. As discussed above, this is typically only a small fraction of the total number of particles of the same size (i.e. within the size range defined by the diameter channel) residing in the volume of sample suspension that passed through the sensor during data collection. This fraction, $phi_d$, of particles actually detected by the new LE- (or LS-) type sensor varies significantly with the particle diameter, d.

The third procedure involves multiplying the number of particles contained in each diameter channel of the raw PSD by the value of $1/phi_1$ that applies for that channel. This operation yields the final, desired PSD, describing the number of particles of each size estimated to reside in the quantity of sample suspension that passed through the sensor during data acquisition. Values of $1/phi_d$ for each value of diameter, d, can be obtained from the sensor efficiency curve, $phi_d$ vs d, by interpolation.

There are two independent algorithms presented herein for deconvoluting a measured PHD, to obtain the dPHD, hereinafter referred to as "matrix inversion" and "successive subtraction." Implementation of either procedure is based on the property that the response of the new LE- (or LS-) type sensor—like its conventional SPOS counterpart—is additive. Because the particles passing through the sensor give rise to signal pulses one at a time, the resulting PHD can be considered to be composed of a linear combination, or weighted sum, of individual PHDs corresponding to uniform particles of various sizes, referred to as "basis vectors." (This term is well known in linear algebra.) Each of these basis vectors represents the response of the system to a statistically significant number of particles of a single, given size.

In one embodiment, the focused light scattering device described herein incorporates both the new LE- and LS-type SPOS sensors in a single sensor, having two independent output signals, $V_{LE}$ and $V_{LS}$. The resulting dual "LE+LS" design offers increased capability and flexibility, providing single-particle counting and sizing over a relatively large range of particle sizes. The LS-type sensor subsystem can be used to extend the size range below the lower detection limit provided by the new LE-type sensor subsystem. The extent to which the lower particle size limit can be extended depends on a variety of parameters. These include: the width, 2w, of the narrow (typically focused) beam within the measurement flow cell; the power of the light source; the range of angles over which scattered light is collected for implementation of the new LS-type sensing function; and the physical properties, including the refractive index, of both the particles and the suspending fluid.

The dual LE+LS sensor includes a light source, preferably consisting of a laser diode module, typically having an output wavelength in the range of 600 to 1100 nanometers (nm). The beam produced by the light source means preferably is collimated (parallel) and "circularized"—i.e. the intensity is a function only of the distance, r, from the central axis. Furthermore, the beam preferably has a Gaussian intensity profile, along any axis normal to the axis of propagation of the beam. The new LE+LS sensor also includes a focusing means, typically a single- or multi-element lens, capable of focusing the starting collimated light beam to the desired beam width, 2w, at the center of the measurement flow channel in the OSZ, consistent with the desired particle size range. It is assumed that the focusing means has an appropriate focal length, thus yielding acceptable values for both the width and depth of field of the focused beam. The latter is preferably significantly longer than the thickness, b, of the flow channel, in order to optimize the resolution of the resulting PSD.

A measurement flow cell is typically fabricated from a suitable transparent material, such as glass, quartz or sapphire, or alternative semi-transparent material, such as PTFE (e.g. Teflon™, manufactured by DuPont) or other suitable plastic that is sufficiently transparent at the operating wavelength and compatible with the fluid-particle mixture. A suitable fluidics system, including a flow pump means and optional means for automatic dilution of the starting sample suspension (if needed), are typically required to facilitate the steady flow of the particle-fluid suspension through the flow cell. The flow rate, F, is usually chosen to be the same as, or close to, the value used to generate the calibration curve for the LE- or LS-type sensor.

The thickness, b, of the flow channel should be small enough to achieve a high coincidence concentration limit and as uniform a beam width as possible (ideally with b<<depth of field), resulting in improved resolution for the final PSD. However, it must be large enough to prevent frequent clogging by over-size particles (e.g. agglomerated primaries and contaminants in the fluid/diluent). The width, a, of the flow channel is also chosen to strike a compromise between two competing effects. A relatively large value reduces the impedance to the flowing fluid-particle mixture and lowers the velocity (and increases the pulse width) for a given flow rate, F. However, the larger parameter a, the smaller the sensor efficiency, $phi_d$, for any given particle diameter, d. This results in a smaller fraction of particles in the sample actually contributing to the measured PHD and final PSD, which, if too small, may be undesirable.

The new LE+LS sensor contains two separate light collection and detection subsystems, used independently to extract the desired LE- and LS-type signals. The LE-type signal can be captured using a small light reflecting means M (e.g. mirror), positioned so as to intercept the narrow beam of incident light after it passes through the flow cell and fluid-particle mixture. The resulting transmitted beam, thus deflected away from the optical axis of the combined sensor, is caused to impinge on a nearby light detection means $D_{LE}$. The latter typically consists of a small-area, solid-state (silicon) detector, operating in a linear region and having a spectral response that is matched to the wavelength of the light source, thus providing an output signal with an acceptable signal/noise (S/N) ratio. The output of the detector means is typically a current (the "photocurrent"), which can be conditioned by a current-to-voltage converter ("transimpedance" amplifier), yielding an output signal in the generally desired form of a time-varying voltage, $V_{LE}(t)$.

Alternatively, a small detector element can be placed directly in the path of the light beam after it emerges from the flow cell, thus eliminating the need for the intermediate light reflecting means discussed above. Regardless of whether a mirror or detector element is used to "capture" the transmitted light beam, there are two requirements. First, the means used must function as an effective beam "stop." That is, it must be able to prevent any significant fraction of the arriving light flux from being reflected back toward the flow cell, thus becoming a source of "stray" light. Through unintended internal reflections from the various optical surfaces, a portion of the stray light can find its way to the scattering detection means $D_{LS}$, thus corrupting the resulting LS signal, by contributing a portion of the incident intensity to the latter. Second, the means used to capture the LE signal must be small enough not to intercept, and therefore block, scattered light rays at any angles that are intended to be captured and redirected to the light detection means $D_{LS}$, as discussed below.

Separately, scattered light originating from particles passing through the OSZ is collected over a range of scattering angles, theta, with $theta_1$<theta<$theta_2$, where angles $theta_1$ and $theta_2$ are defined by a suitable aperture means, such as an annular mask fabricated from a photographic negative with an outer opaque portion, a transparent intermediate portion, and an inner opaque portion. The scattered rays selected by the mask are allowed to impinge on a collecting lens of appropriate focal length and location, which converts the diverging scattered rays into an approximately parallel beam. A second lens is then typically used to refocus the rays onto a relatively small light detection means $D_{LS}$. As in the case of the LE subsystem, the output signal of $D_{LS}$ is typically a current, which can be optionally conditioned, typically by means of a transimpedance amplifier, so that the final output is in the form of a time-varying voltage, $V_{LS}(t)$.

The signals $V_{LE}(t)$ and $V_{LS}(t)$ can be organized into respective pulse height distributions PHD by pulse height analyzers. The PHDs are then respectively deconvoluted in computer deconvolution means, which ultimately compute a pair of respective particle size distributions ("PSD").

This embodiment can be implemented as an LE-type or LS-type sensor only, simply by removing (or not installing in the first place) the optical elements, detection means and signal conditioning circuitry associated with the unwanted subsystem. In this case, it may be useful to adjust the width, 2w, of the focused beam within the measurement flow channel, in order to optimize the resulting performance of the LE- or LS-type sensor. This parameter will impact the usable particle size range, coincidence concentration limit and minimum detectable particle size differently for the two sensing modes, as discussed earlier.

Hydrodynamic Sample Injection

In one embodiment, the apparatus uses hydrodynamic sample injection, such as is described in Pelssers et al., Journal of Colloid and Interface Science, Volume 137, Issue 2, July 1990, Pages 350-361. Colloidal dispersions, such as platelets in serum or other media, can be hydrodynamically focused laser. into a narrow stream, with widths ranging from about 3 to about 10, preferably about μm width. The use of a focused light scattering technique allows one to measure relatively small particle sizes. However, where a focused beam hits particles in a relatively wide sample stream (as described above, where the beam is narrower than the measurement flow channel in the width direction), the detection method relies somewhat on statistics. That is, where the beam is substantially narrower than the sample stream, an assumption is made that there is an equal distribution of particles in the sample stream, so that one can extrapolate the results of the interaction of the light in the narrow beam with the particles in its path over the entire width of the sample stream. By hydrodynamically focusing the sample into a stream with a relatively narrow width, and using a focused light source, it is possible to count all or most of the particles in the sample stream, and rely to a lesser extent on statistics.

Figure 3:
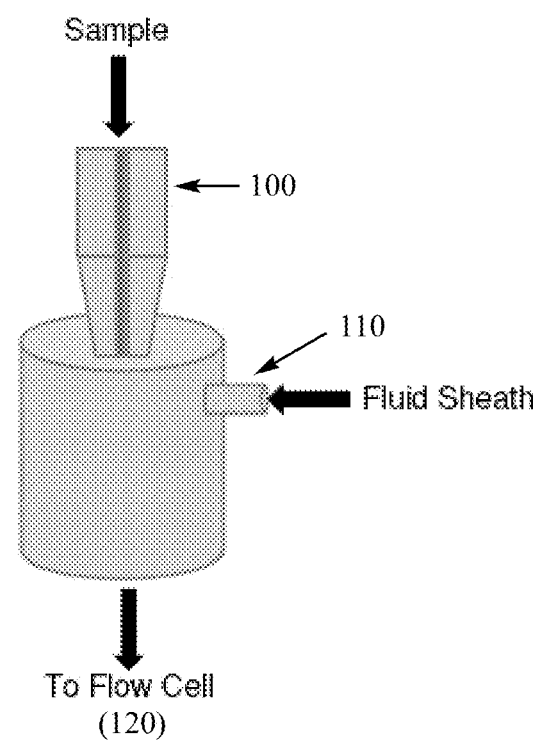
FIG. 3 is a schematic illustration of a hydrodynamic flow injector.

A representative injector for carrying out hydrodynamic injection is shown in more detail in FIG. 3. As shown in FIG. 3, As shown in FIG. 3, a sample passes through an inlet port (100), through a fluid sheath (110), and outward through the bottom of the injector into a flow cell (120). The sample travels through the sample injection tube, with fluid from a fluid sheath surrounding the stream, and hydrodynamic focusing within the flow cell forcing particles into a single-particle-file stream where laser light intercepts the stream at a sample interrogation point. The design of the flow cell, when a hydrodynamic injector is used, permits particles to flow through the center of the flow cell. Increasing the sample pressure increases the core diameter and the flow rate.

The device described herein is similar to the device disclosed in U.S. Patent Application Publication No. 20040011975, the contents of which are hereby incorporated by reference in its entirety. The main differences between the device disclosed in U.S. Patent Application Publication No. 20040011975 and the instant device are that the instant device further includes a hydrodynamic injector, or additional lasers and detectors, such as detectors that can detect fluorescent labels.

The apparatus is described therein is useful in performing particle analysis using focused light scattering techniques. However, as described herein, other similar apparatus can be employed, including detectors for focused light scattering and/or light extinction.

The principal defining characteristic of the focused light scattering method described herein is not simply a significant reduction in the size of the illuminated area, $A_O$, resulting in a significant reduction in $V_{OSZ}$ and improvement in sensitivity. Rather, it concerns the nature of the illuminating beam and the resulting OSZ thereby defined.

The term "focused light scattering" refers to a method for sensing single particles, suspended in a solution, when the solution is passed through a focused beam. When the beam passes through the solution without being scattered by a particle, the beam passes on to a photodetector and the intensity is measured. When the beam is scattered, in whole or in part, by a particle, the intensity of the beam hitting the photodetector is altered. The particle size and concentration can be calculated, for example, using light-extinction, light-scattering detection, or both.

In one embodiment, the beam is produced by a laser. The laser beam interacts with the particles, and produces scattered light when the laser beam interacts with a particle. In one aspect of this embodiment, the apparatus includes two or more different lasers, which can give off light at two or more different wavelengths, and/or which can interact with the particles at different angles. The use of light at different wavelengths can enable one to identify specific epitopes. Particles can interact with specific molecules, including fluorescently-labeled molecules, and the fluorescence can be detected using a laser with light at a predetermined wavelength that interacts with the fluorescent label. The use of more than two lasers can enable the use of two or more fluorescent labels, which labels fluoresce at different wavelengths. This technique is described in more detail below.

A beam of light (usually laser light) of a single wavelength is directed onto a stream of a fluid, in one embodiment, a hydrodynamically-focused stream of a fluid, which includes particles whose size and number is to be determined.

A number of detectors are aimed at the point where the stream passes through the light beam. In one aspect of this embodiment, one detector is in line with the light beam (Forward Scatter or FSC) and one or more detectors are perpendicular to it, including Side Scatter or SSC detectors and one or more fluorescent detectors. Each suspended particle passing through the beam scatters the ray, and fluorescent chemicals either present within the particle or attached to the particle are excited into emitting light at a longer wavelength than the light source. This combination of scattered and fluorescent light is picked up by the detectors, and, by analyzing fluctuations in brightness at each detector (one for each fluorescent emission peak), it is then possible to derive various types of information about the physical and chemical structure of each individual particle.

Thus, in some embodiments of the apparatus described herein, there are three or more detectors. For example, one can include one detector for extinction [useful for measuring particles with a size >0.7 microns], one for scattered light [useful for measuring particles with a size between 0.15 and 0.7 microns] and one or more for determining fluorescence [used for phenotyping].

Light Sources

The sources of light can include lamps (i.e., mercury, xenon); high-power water-cooled lasers (i.e., argon, krypton, dye laser); low-power air-cooled lasers (i.e., argon (488 nm), red-HeNe (633 nm), green-HeNe, HeCd (UV)); diode lasers (i.e., blue, green, red, violet). The detectors can convert fluorescence signals from light into electrical signals that can be processed by a computer.

Data Acquisition

The process of collecting data from samples is termed "acquisition." Acquisition is typically mediated by a computer physically connected to the apparatus, and the software which handles the digital interface with the apparatus. The software is capable of adjusting parameters (i.e. voltage, compensation, etc.) for the sample being tested, and also assists in displaying initial sample information while acquiring sample data to insure that parameters are set correctly. An interactive database can allow the apparatus to be used in applications for both clinical and research purposes. A wide variety of analysis software and fluorescently-labeled antibodies has been developed, and are well known to those of skill in the art.

The apparatus can include multiple lasers (between 2 and 5, typically between two and four) and fluorescence detectors (typically between 2 and 18, more typically between 2 and 10). Increasing the number of lasers and detectors allows for multiple antibody labeling, and can more precisely identify a target population by their phenotypic markers.

Gating

The data generated by the apparatus can be plotted in a single dimension, in two dimensions, or even in three dimensions. The regions on these plots can be sequentially separated, based on fluorescence intensity, by creating a series of subset extractions, termed "gates." Specific gating protocols exist for diagnostic and clinical purposes especially in relation to hematology.

The plots are often made on logarithmic scales. Because different fluorescent dyes' emission spectra overlap, signals at the detectors have to be compensated electronically as well as computationally. Data accumulated using the apparatus can be analyzed using software, e.g., Flowjo, FCS Express, VenturiOne or CellQuest Pro. Data analysis can be performed on a separate computer, if desired.

Computational Analysis

Automated population identification using computational methods can be used as an alternative to traditional gating strategies. Automated identification systems can potentially help find rare and/or hidden populations. Representative automated methods include FLOCK in Immunology Database and Analysis Portal (ImmPort), FLAME in GenePattern and flowClust, in Bioconductor.

Microfluidics

In some applications, particularly clinical applications, it can be desirable to use microfluidics to introduce samples to the apparatus. The microfluidic device can be disposable (i.e., used once or perhaps a few times, followed by disposal and replacement) and/or composed of a polymeric material. The microfluidic device can be adapted to reduce the amount of sample used to determine whether a patient can benefit from a particular therapy. The microfluidic device preferably provides a tip adapted for delivering the biological sample including the platelets into the cell through which light passes, so that the platelets can then travel through the light beam(s). In some embodiments, the tip is adapted for sheath spraying. In other embodiments, the tip is adapted for non-sheath spraying. In any of the embodiments herein the apparatus may include a disposable inlet capillary.

Auto-Diluters

The apparatus can also include an autodiluter, which can start with the most dilute sample, rather than the most concentrated sample, and can therefore use less sample. Autodiluters are well known to those of skill in the art. Representative autodiluters include the AutoDiluter-5.2, the CETAC ADX-500 Autodiluter, the ProLiquid AutoDiluter, and the DYNATECH Autodiluter III.

Mechanical Shearing Devices (For EQELS and/or ISADE Devices)

Certain biological and non-biological species require mechanical shear for activation. Species may be a cell, a protein, ribo- or deoxyribonucleic acid, polysaccharides, aggregated cells or molecules or the like. Representative examples of cells include, but are not limited to, endothelial cells and platelets, and representative examples of molecules include von Willebrand factor and DNA. Both biological and non-biological species may aggregate to exhibit an effect on the mechanical properties of a fluid. Examples would be thixotropy (shear thinning) and rheopexy (shear thickening). Biological cells, molecules like fibrin, vWF, tubulin, myosin, and the like, and non-biological materials, like paints or inks, are examples.

Figure 4:
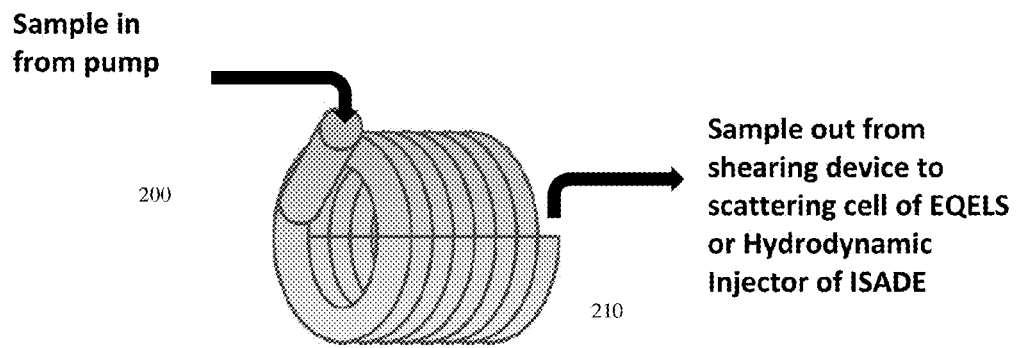
FIG. 4 is a schematic illustration of a device to apply precise mechanical shear to a sample.

The provision of mechanical shear can be accomplished by integrating a mechanical shearing device into the apparatus described herein. Although there are many means for introducing mechanical shear, any one of which can be used, in one embodiment, a suitable device is shown in FIG. 4. In this device, a sample is placed in a suitable container. The sample in the container may then be extricated from the container manually, or by a robotic and then introduced into a pump. In one aspect of this embodiment, the pump is a precision pump that can produce a precise and continuous flow rate of the sample within the shearing device (200). The shearing device (200) is composed of a hollow fiber that may be linear or coiled, though in the embodiment shown in FIG. 4, it is coiled. In one aspect of this embodiment, the hollow fiber is composed of materials that minimize interaction with the sample or under certain other cases or circumstances may interact with the sample in a specific manner. For example, the inner surface of the hollow fiber may be coated with collagen that interacts with vWF or with platelets. The length of the hollow fiber and the inter diameter of the hollow fiber can be precisely known. Further, the pressure drop across the fiber can be precisely known, from the flow rates, volume flux, and/or from pressure sensors located at each end of the hollow fiber. From these data, the mechanical shear rate experienced by the sample can be calculated. The effluent sample can then be passed on to the scattering chamber of EQELS or the hydrodynamic injector of the ISADE device described herein by means of a linking hollow fiber. In this manner, the entire system is closed, and the sample can pass in a continuous manner from the original sample container though the shearing device and into the respective scattering chambers or hydrodynamic injector, then into an effluent chamber via an exit port (210).

Figure 5:
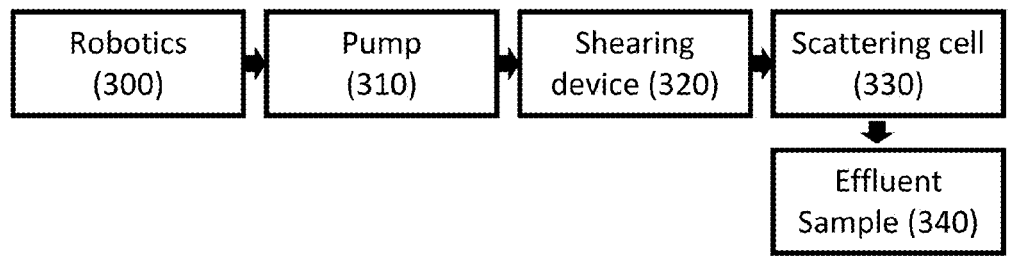
FIG. 5 is a flow chart showing the path of a fluid sample from a pump controlled by robotics, through a shearing device, to a scattering cell, where dynamic light scattering or electrophoretic light scattering can be measured, to where the sample leaves the device as effluent.

In use, the sample follows a path from a storage device, via a pump (310) controlled by robotics (300) through a shearing device (320), into a cell where scattered light can be detected (330), and then to an effluent container (340). Although a scattering chamber of an EQELS device is shown in FIG. 5, when the shearing device is used in connection with the hydrodynamic injector of an ISADE device as described herein, the hydrodynamic injector can substitute for the scattering chamber shown in FIG. 5.

In an alternative embodiment, shear can be provided using ultrasound; vibration; radiowaves; cone-plate, parallel plate or coutte shearing surfaces; a coaxial plunger device and the like).

Robotics

In high-throughput screening, it can be preferable to include robotics, which can introduce the samples to the apparatus. Ideally, the apparatus can then be cleaned in between samples, for example, by flushing the various lines, and subsequent samples introduced, enabling the screening to be automated. Information on the screening results can be stored, for example, in a memory map, and the information correlated with the patient's identity.

A "focused light scattering device" is a single-particle optical sensor, which has high sensitivity and responds to relatively concentrated suspensions, uses a relatively narrow light beam to illuminate an optical sensing zone non-uniformly. It differs from conventional single particle optical sizing (SPOS) devices in that it can handle more concentrated solutions and smaller particle sizes.

In use, a solution including suspended particles passes through a zone. The zone is smaller than the flow channel, so that the sensor responds to only a fraction of the total number of particles flowing through the channel, detecting a statistically significant number of particles of any relevant diameter.

Because different particle trajectories flow through different parts of the zone illuminated at different intensities, it is necessary to deconvolute the result. Two methods of deconvolution can be used: modified matrix inversion or successive subtraction. Both methods use a few basis vectors measured empirically or computed from a theoretical model, and the remaining basis vectors are derived from these few. The sensor is compensated for turbidity.

The sensor apparatus for single-particle optical sizing of particles in a fluid suspension typically includes a means for establishing flow of the suspension through a physically well-defined measurement flow channel. There is also an illumination means for effectively directing a relatively narrow beam of light, having an axis, through the measurement flow channel to form an optical sensing zone within the measurement flow channel. The beam of light and the optical sensing zone are of such size relative to the size of the measurement flow channel that the sensor apparatus responds to only a fraction of the total number of particles flowing through the measurement flow channel. In this manner, the sensor apparatus responds effectively to a relatively concentrated fluid suspension.

The beam has a maximum intensity portion and a continuum of lesser intensities for positions spaced transverse to the axis from the maximum intensity portion. In this manner, some of the particles have trajectories through the maximum intensity portion, others of the particles have trajectories through the lesser intensity positions, and still others of the particles may have trajectories outside the zone. Typically, the maximum intensity portion of the beam is in a central portion of the beam.

The device also includes a detector means for photo-detecting light from the zone to provide pulse height signals. These signals each respond to a particle flowing through the zone. The pulse height signals are functions of the sizes and trajectories of detected particles. Particles of a given size provide a maximum pulse height signal when flowing through the maximum intensity portion, and lesser pulse height signals when flowing through the lesser intensity positions of the zone. The pulse height signals, collectively, form a pulse height distribution PHD.

The device further includes a means for mathematically deconvoluting the pulse height distribution to extract a particle size distribution of the PSD particles in the fluid suspension. The sensor apparatus can detect a statistically significant number of particles of any given diameter or range of diameters that are relevant to the fluid suspension.

In one embodiment, the measurement flow channel has a thickness dimension axially of the beam of light, a width dimension transverse to the beam, and a flow direction substantially perpendicular to the thickness and width dimensions. The beam is narrower than the measurement flow channel in the width direction. The beam can be focused with a depth of field which is substantially larger than the thickness dimension, and the beam substantially has an effective width which does not vary substantially over the thickness dimension.

In another embodiment, the beam has an effective width between opposing positions transverse to the axis in the beam, at which the lesser intensities have fallen to a given fraction of the maximum intensity. The effective width is chosen so that the largest particles of interest can be effectively sized. The given fraction can be, for example, $1/e^2$ of the maximum intensity, where e is the base of the natural system of logarithms, and the effective width is substantially one half the size of the largest particle to be sized.

The light beam can have, for example, a Gaussian intensity profile, a circular cross-section, or an elliptical cross-section being wider in a direction transverse to particle flow.

The detector means can be include a light extinction-type detector, and can be a combination of detectors, for example, a light-extinction detector type and a light-scattering type detector. The light-scattering type detector means can include means for passing a portion of scattered light from the zone through a mask to select light scattered between a first and a second angle to the beam and a means for directing a portion of the light transmitted through the zone to a light-extinction type detector.

The detector means can include a mirror for deflecting a portion of the light from the optical-sensing zone to the light-extinction detector. The illuminating means can include a light source and optical fiber means for conveying light from the light source to the optical sensing zone, and projecting the light through the zone.

The detector means can also include an optical fiber means for conveying the light passing through the optical sensing zone to the light-extinction type detector. The detector means can also include means for passing a portion of the light scattered from the zone through a mask, to select light scattered between a first and second angle to the beam, and an optical fiber means for conveying the portion of the light to a light-scattering type detector. The detector means can also include a light-scattering detector.

In one embodiment, the illumination means provides two light beams directed through a pair of optical sensing zones positioned within the measuring flow channel, and each beam has an effective width determined by a desired maximum particle size.

The detector means can include a light-scattering detector and a means for passing light scattered from the zone through a mask means. The mask means can include a plurality of masks and means for selecting one of the masks for passing the light scattered from the zone, each mask defining different angles between which the light is scattered. The masks can be located on a rotatable wheel, and a mask can be selected by rotating the wheel to a desired position.

The illuminating means can project a relatively wide collimated beam through the optical sensing zone, and can include an acceptance aperture to capture only those light rays that closely surround the axis of the beam. This reduces the effective width of the beam to a width in a direction transverse to the axis of the light beam which is substantially one-half the size of the largest particle to be sized. The illuminating means can also include a means for coupling the light rays to the detector means. This can be, for example, an optical fiber means.

In one aspect of the invention, a statistically significant number of particles of each relevant size flow through all portions and positions of the zone.

In another aspect of the invention, the fluid suspension is relatively concentrated and the apparatus further comprises means to compensate for turbidity of the suspension. In this aspect, the detector means can operate on a light extinction principle, and provide a signal having a baseline voltage level. The pulse height signals appear as downwardly extending pulses from the baseline voltage level, and the means for compensation for turbidity of the suspension can include means to sense the baseline voltage level and automatically increase the level to approximately the baseline voltage level present in the absence of turbidity in the suspension. The detector means can operate on a light extinction principle, and provide a signal having a baseline voltage level, wherein the means to compensate for turbidity can include a computer means for correcting the pulse height signals in response to the ratio of the baseline voltage level when the fluid suspension is not turbid, to the baseline voltage level for the turbid fluid suspension.

The detector means can also operate on a light extinction principle and provide a signal having a baseline voltage level, wherein the means to compensate for turbidity includes a means to adjust the intensity of the beam of light by increasing the amount of light produced by the illuminating means in response to the ratio of the baseline voltage level when the fluid suspension is not turbid, to the baseline voltage level for the turbid fluid suspension.

The particle trajectories can be substantially uniformly distributed across the width of the measurement flow channel.

Deconvoluting the Pulse Height Distribution

The means for deconvoluting the pulse height distribution can include basis vectors, each corresponding to a particular particle size, and a source vector representing a measured pulse height distribution for a fluid suspension as detected by the detector means. There can also be a means using a deconvolution algorithm to derive the particle size distribution from the pulse height distribution. At least some of the basis vectors can have values based upon measurements of particles of known size. Some of the basis vectors can also have values based upon measurements of particles of known size and others of the basis vectors can be computed from the sum of the basis vectors by interpolation and/or extrapolation.

The basis vectors can be computed, and the basis vectors can be column basis vectors of a matrix, where the means using a deconvolution algorithm performs matrix inversion and vector multiplication, or the means using a deconvolution algorithm can perform successive subtraction.

The means using a deconvolution algorithm can provide a deconvoluted pulse height distribution dPHD, and the apparatus further comprises means providing a calibration curve of the relationship of pulse height and diameter, and means using the calibration curve to transform each deconvoluted pulse height value in the dPHD into a unique particle diameter associated with this pulse height value. This can yield a "raw" particle size distribution PSD. There can also be a means for converting the raw PSD into a final PSD by renormalizing the raw PSD by multiplying by the value 1/$PHI_d$, where $PHI_d$ is the fraction of particles actually detected by the device for particles of each size.

The particle trajectories can be distributed non-uniformly across the width of the measurement flow channel, and the basis vectors can be based upon the response of particles of known size flowing through the measurement flow channel with the same non-uniform distribution of particle trajectories as the fluid suspension.

The sensor apparatus may respond only to a fraction of the total number of particles flowing through the measurement flow channel.

One can prepare a matrix for deconvoluting pulse height distributions derived from particles of unknown size flowing along different trajectories through a non-uniform light field of a single-particle optical sizing device. This can enable one to size particles in a fluid suspension. To do this, one can determine the value of at least one empirical basis vector for the matrix by measuring the response of particles of known size flowing through the single-particle optical sizing device. Then, one can compute other basis vectors for the matrix corresponding to particles of other sizes, by interpolating and/or extrapolating the other basis vectors from the empirical basis vector.

One can also determine the value of additional empirical basis vectors for the matrix by measuring the response of particles of known sizes flowing through the single-particle optical sizing device, and computing the other basis vectors for the matrix corresponding to particles of other sizes from the at least one empirical basis vector and the additional empirical basis vectors.

Another way to prepare a matrix for deconvoluting pulse height distributions derived from particles of unknown size flowing along different trajectories through a non-uniform light field of a single-particle optical sizing device for sizing particles in a fluid suspension involves determining the value of at least one computed basis vector corresponding to particles of at least one size for the matrix. One can compute other basis vectors for the matrix corresponding to particles of other sizes from computed basis vectors.

Also disclosed is a method of deconvoluting a pulse height distribution derived from particles of unknown size flowing along different trajectories through a non-uniform light field of a single-particle optical sizing device for sizing particles in a fluid suspension. The method involves setting up a matrix having a plurality of columns, each containing a basis vector comprising a pulse height distribution of particles of a known size corresponding to the response of a photo-detector of the device to the particles of known size. Each successive column contains a basis vector for particles of successively larger sizes. The matrix also has a like plurality of rows, each corresponding to a successive pulse height channel, each channel including a range of pulse heights, with successive rows corresponding to successively larger pulse heights, and with each column having a maximum count pulse height value at a location for a row which relates to a pulse height corresponding to the particle of known size associated with the column. The maximum count pulse height values for successive columns are arranged on a diagonal of the matrix. The matrix is modified by setting all terms corresponding to pulse height values greater than the maximum count pulse height value in a column to zero. A deconvolution algorithm is used to perform matrix inversion and vector multiplication of the pulse height distribution and the matrix as modified.

Before the modifying step, one can renormalize the values of the basis vectors in the columns by setting the maximum count pulse height value to equal 1.0 and all other count pulse height values in the column to a value maintaining the same proportionate value to 1.0 that the other count pulse height values had to the maximum count pulse height value of the column.

The response of the photo-detection to the particles of known size is developed empirically for some of the basis vectors by sending particles of the substantially known size through the device and providing a response by the device to the particles of known size. The response to the photo-detector for the remaining basis vectors can be computed by interpolating and/or extrapolating the response for the remaining basis vectors from the some of basis vectors.

The response of the photo-detector to the particles of known size can be computed for some of the basis vectors and the response to the photo-detector for the remaining basis vectors can be computed by interpolating and/or extrapolating the response from the some basis vectors.

A pulse height distribution ("PHD") can be derived from particles of unknown size flowing along different trajectories through a non-uniform light field of a single-particle optical sizing device for sizing particles in a fluid suspension can be deconvoluted by setting up a matrix having a plurality of columns. Each column includes a basis vector comprising a pulse height distribution of particles of a substantially known size corresponding to the response of a photo-detector of the device to the particles of known size, and each successive column contains a basis vector for particles of successively larger sizes. The matrix can also include a like plurality of rows, each corresponding to a successive pulse height channel, each channel including a range of pulse heights, successive rows corresponding to successively larger pulse heights, each column having a maximum count pulse height value at a location for a row which relates to a pulse height corresponding to the particle of known size associates with the column. The maximum count pulse height values for successive columns can be arranged on a diagonal of the matrix. A successive subtraction algorithm can be implemented, by starting with the basis vector with its maximum count value in the largest row number; scaling a column basis vector by a factor corresponding to the value of the row in the PHD that matches the column number; subtracting the scaled basis vector from the PHD to form an element of a deconvoluted PHD (dPHD), leaving an intermediate PHD vector with a smaller number of total particles; and repeating this process using the remaining basis vectors until the entire PHD has been consumed and all the elements of the deconvoluted dPHD have been formed.

A single-particle optical sizing sensor for sizing particles in a relatively concentrated fluid suspension sample for turbidity of the suspension sample can be compensated using a sensor operating on a light extinction principle whereby a photo-detector produces signal $V_{LE}(t)$ having a baseline voltage level and a response to blockage of light by a particle as a downwardly extending pulse from the baseline voltage level. The compensation method involves passing a non-turbid suspension through the sensor; measuring a baseline voltage level $V_0$ produced in response to the non-turbid suspension; passing the relatively concentrated suspension sample through the sensor; measuring a baseline voltage $V_0^T$ produced in response to the relatively concentrated suspension sample, calculating the ratio $V_o V_0^T$; and adjusting the sensor in response to G to compensate for the turbidity when the relatively concentrated suspension sample passes through the sensor.

The baseline voltage $V_0^T$ can effectively be subtracted from the signal $V_{LE}(t)$, the remaining signal can be inverted to produce a pulse height signal 2 $V_{LE}^T(t)$, and an adjustable gain amplifying means can be used to amplify the pulse height signal 3 $V_{LE}^T(t)$. The adjustable gain amplifying means can be controlled by the ratio G to provide a compensated pulse height signal $\Delta V_{LE(t)}$.

The signal $V_{LE}(t)$ produced by the sensor in response to the relatively concentrated suspension sample can be amplified by adjustable gain amplifier means, the gain of which is controlled by the ratio G to provide a compensated signal $V_{LE}(t)$ having a compensated baseline voltage $V_0$, subtracting the baseline voltage $V_0$ from the compensated signal $V_{LE}(t)$, and inverting the remaining signal to produce compensated pulse height signal $\Delta V_{LE}(t)$.

In one embodiment, the single-particle optical sizing sensor comprises a light source producing a light beam of adjustable intensity, wherein the intensity is increased in response to the ratio G to compensate for the turbidity.

Particles in a fluid suspension can also be optically sized by establishing a flow of the suspension through a physically well-defined measurement flow channel of a single-particle optical sizing sensor apparatus wherein a beam of light, having an axis, is directed through the measurement flow channel to form an optical sensing zone within the measurement flow channel. The beam of light and the optical sensing zone are ideally of such size relative to the size of the measurement flow channel that the sensor apparatus responds to only a fraction of the total number of particles flowing through the measurement flow channel. The sensor apparatus can respond effectively to a relatively concentrated fluid suspension. The beam can have a maximum intensity portion in the beam and a continuum of lesser intensities for positions in the beam spaced transversely from the axis, whereby some of the particles have a trajectory through the maximum intensity portion, others of the particles have trajectories through the lesser intensity positions, and still others of the particles may have trajectories outside the zone. Light from the zone can be detected to provide pulse height signals, each responsive to a particle flowing through the zone. The pulse height signals are functions of the sizes and trajectories of detected particles, and the pulse height signals collectively form a pulse height distribution PHD. The PDH can be mathematically deconvoluted and processed to extract from the PHD a particle size distribution PSD of the particles in the fluid suspension.

The step of mathematically deconvoluting the PHD can involve determining the value of at least one empirical basis vector by measuring the response to particles of known size flowing through the single-particle optical sizing device. Other basis vectors corresponding to particles of other sizes can be computed by interpolating and/or extrapolating the other basis vectors from the empirical basis vector.

The value of additional empirical basis vectors for particles of known sizes flowing through the single-particle optical sizing device can be determined; and the other basis vectors for the matrix corresponding to particles of other sizes can be calculated by interpolating and/or extrapolating the other basis vectors from at least one empirical basis vector and the additional empirical basis vectors. The method can further involve determining the value of at least one computed basis vector corresponding to particles of at least one size. Other basis vectors corresponding to particles of other sizes can also be computed by interpolating and/or extrapolating the other basis vectors from computed basis vectors.

The step of deconvoluting and processing the PHD can involve setting up a matrix having a plurality of columns, each containing a basis vector comprising a pulse height distribution of particles of a known size corresponding to the response of a photo-detector of the device to the particles of known size, each successive column containing a basis vector for particles of successively larger sizes. The matrix can also have a like plurality of rows, each corresponding to a successive pulse height channel, each channel including a range of pulse heights, successive rows corresponding to successively larger pulse heights, each column having a maximum count pulse height value at a location for a row which relates to pulse heights corresponding to the particle of known size associated with the column. The maximum count pulse height values for successive columns can be arranged on a diagonal of the matrix. The matrix can be modified by setting all terms corresponding to pulse height values greater than the maximum count pulse height value in a column to zero. A deconvolution algorithm can be used to perform matrix inversion and vector multiplication of the pulse height distribution and the inverted matrix as modified. The response of the photo-detector to the particles of known size can be developed empirically for some of the basis vectors by directing a flow of particles of the known size through the device and providing a response by the device to the particles of known size. The response to the photo-detector for the remaining basis vectors can be calculated by interpolating and/or extrapolating the response for the remaining basis vectors from the some of basis vectors.

The step of mathematically deconvoluting the PHD can also involve using a deconvolution algorithm to provide a deconvoluted pulse height distribution dPHD. The method can further involve providing a calibration curve of the relationship of pulse height and diameter, and using the calibration curve to translate each deconvoluted pulse height value in the dPHD into a unique particle diameter associated with this pulse height value yielding a "raw" particle size distribution in PSD. The raw PSD can be converted into a final PSD by renormalizing the raw PSD by multiplying by the value $1/PHI_d$, where $PHI_d$ is the fraction of particles actually detected by the device for particles of each size.

II. Particles that can be Detected

Using the techniques described herein, various biological particles can be detected. Cells are one type of biological particle that can be detected. The method can be used to determine the presence or absence of a specific type of cell in a given solution. For example, a sample of blood, urine, spinal fluid, and the like can be evaluated for the presence or absence of bacteria, fungi, viruses, and the like. The particle size, and, optionally, particle shape, can also provide information about the specific type of bacteria, fungi or virus.

III. Microparticles and Nanoparticles Suitable for Use in Focused Light Scattering In some embodiments, where the complex between an active agent and a biological particle does not result in a change in particle size (i.e., no particle agglomeration or cell rupture), it may be necessary to conjugate the active agent with a microparticle (such as a nanoparticle, polystyrene bead, gold particle, and the like). Thus, when the agent forms a complex with the biological particle, the complex increases the size of the biological particle by the size of the microparticle, and this increased particle size is measurable using the techniques described herein.

In one embodiment, the particles have a particle size in the range of between about 0.1 and 10 μm, and ideally have a relatively consistent amount of active agent bound to them. That is, if all that is important is to determine that the biological particles bound to an active agent of interest, then one can simply incubate the biological particle with the conjugate, and look for the decrease in peak corresponding to the biological particle. This will confirm that a complex of the biological particle and the active agent was formed.

If there is an interest in quantifying how much of the biological particle was present, then it may be important to use particles with a nearly uniform particle size, defined as having 90% or more of the particles within 5% of the mean particle size, more preferably around 99% uniformity or better. In addition to a uniform particle size, in some embodiments, it may be desirable to have uniform substitution on the particles themselves. That is, rather than having particles of a relatively uniform particle size form complexes of different particle sizes with the biological particle of interest, it may be desirable to form complexes with a relatively uniform particle size, to ease their quantification.

One way to produce particles with a relatively constant particle size, and with a relatively consistent amount of active agent conjugated to the particles, is to use dendrimers. The dendrimers can include a known quantity of the active agent, by virtue of the active functional groups at the terminus on the dendrimers.

Another way is to produce polymer particles with: a) a relatively narrow size distribution, and b) a relatively consistent amount of protected functional groups, so that after the polymers are produced, the protecting groups can be removed, and the functional groups used to conjugate the polymer particles to an active agent.

The active agent can be conjugated with the particle in such a way that the portion of the active agent that is known to be active (i.e., binds a receptor) is not significantly sterically hindered by its conjugation with the particle. In some embodiments, this will involve preparing an analogue of the active agent which includes a further functional group which can be attached to the particle.

In one embodiment, metallic particles, such as gold particles, are used. Because these particles scatter a significant amount of light, they can be conjugated with a specific active agent, and used to identify even small molecules that bind to the agent. That is, the amount of light that the particle scatters is sufficiently large that the binding of the agent to the molecule of interest can be measured, even though the molecule is not within the size range of biological particles that can be measured. Means for conjugating active agents to metallic particles are known to those of skill in the art.

Metallic particles, such as gold particles, can also be used. These can be conjugated with active agents using known methodology to form particles capable of forming a complex with a biological particle, including particles too small to detect using focused light scattering techniques. Because the particles are highly dense, they produce enough light scattering to be detected, despite their small size. Binding of even a small molecule to the particles can be detected because of the intense scattering from the metallic bead so that enough light is scattered for the complex formation to be measured.

IV. Methods for Detecting the Presence or Absence of Specific Particles in a Solution A sample medium can be evaluated for the presence or absence of specific particles. For example, a sample of blood, urine, spinal fluid, amniotic fluid, pleural fluid, peritoneal fluid and the like, can be evaluated for the presence or absence of specific microbes (cells (lymphocytes, B-cells, T-cells, neutrophils, monocytes, and the like), bacteria, fungi, viruses, and the like), and/or for the presence of relatively high concentrations of white blood cells or other biological particles indicative of a disease state. The methods also permit one to determine presence or absence of shed particles.

The particle (intact cell, microparticle, bacteria, virus, fungus, and the like) can be further identified and characterized by addition of probe particles that are coated with a specific agent that recognizes and binds to the specific surface epitope on the unknown particle surface. If the recognition and binding of the probe particle occurs, a new particle size will be created and appear, thus identifying the unknown particle. For example if the unknown particle was a stem cell and the probe particle was labeled with an anti-CD34 antibody, binding of the probe particle with the stem cell would occur and a new sized particle would appear that would identify the presence of CD34 positive stem cells.

Once the particles are identified by size, one can confirm the identity of the particles, for example, by using a reference library correlating the particle size to a given biological species. Thus, in one embodiment, the method involves comparing information obtained on a biological particle using focused light scattering techniques, with a library of data on biological particles obtained using similar focused light scattering techniques. The library can include information on two or more biological particles, preferably, ten or more particles, more preferably, one hundred or more particles, and, most preferably, more than a thousand particles.

After a preliminary identification has been made on the type of biological particle, other biological techniques can optionally be used to confirm the identity of the particle. For example, an EQELS spectra of the particle can be taken, and compared to a library of EQELS spectra of known particles, to confirm the identity of the particle.

Antibodies or other molecules specific for the specific biological particle can be added to the solution, and if the particles bind to the antibodies, the method will detect the absence of the particles. Ideally, the molecules will be conjugated with a microparticle or nanoparticle, such as a latex particle. As the conjugate interacts with a biological particle, peaks representing the particle and the conjugate will decrease, and peaks corresponding to the complex of the particle and the conjugate will increase.

In one embodiment, the biological particle is a microbe. The technique can be used to identify the type of microbe (i.e., bacteria, fungi, or virus), and, ideally, the specific class of microbe (i.e., Pneumonia, Clostridia, and the like). In this embodiment, once a preliminary identification of the microbe is made, a confirmation assay can be conducted by first taking an EQELS spectra of the microbe in solution, subjecting the microbe to an antibody specific for the microbe, and taking a second EQELS spectra. If the EQELS spectra are different, this provides confirmation that the microbe was properly identified and was bound by the antibody. Further, once a microbe has been identified, a putative antimicrobial compound can be put in solution/suspension along with the microbe, to determine whether it is able to kill the microbe.

In one embodiment, the methods can be used to identify a potential therapeutic agent capable of interacting with a known cell, such as a cancer cell, bacteria, fungi, or virus. In this embodiment, one first uses focused light scattering techniques to generate a spectrum showing the particle size and distribution for the known cancer cell, bacteria, fungi, or virus in a sample medium. Then, a putative therapeutic agent conjugated to a microparticle or nanoparticle is added to the sample medium and allowed to incubate with the known cell, microbe or virus. A second spectrum is generated using focused light scattering techniques. If peaks corresponding to a complex of the microparticle-conjugated therapeutic agent and the known cell or microbe are observed, then the therapeutic agent has bound to the cell. This is indicative of the potential utility of the putative therapeutic agent against the known cell, microbe or virus.

In one aspect of this embodiment, spectra of a microbe in a sample medium are compared with a reference database of spectra of known microbes, thus providing a rapid means for identifying a particular microbe. The spectra can also provide an initial determination of particle size and/or particle density in the medium.

Bacterial Detection

In one example of identifying microbes, one can determine whether the microbes are mono-dispersed or poly-dispersed by their number and size. Since *E. coli* tend to mono-disperse and *Streptococcus* tend to poly-disperse, this embodiment can be used to observe particle size in a sample, where observation of clumping identifies presence bacteria known to clump (i.e. *Streptococcus*).

Detection of Particle Shedding:

In another embodiment, the method is used to detect particle shedding. Representative biological particles which shed smaller particles include tumors, red blood cells, white blood cells, granulocytes, platelets, monocytes, neutrophils, lymphocytes, endothelial cells, cancer cells, stem cells, bacteria, viruses, and fungi. Particle shedding may result from cell interactions, a change of cellular state such as activation or deactivation, as a result of expression, cell death, etc. The methods described herein can be used to identify such particle shedding.

In one embodiment, a drug or ligand is added to a vessel with a cell. Where the drug or ligand reacts with the cell, the cell may shed membrane particles or other particles. As described in detail herein, the method can be used to detect the size, number and/or type of particles shed by the reaction. Therefore, where the cell is known, this technique may be used to detect efficacy of unknown drug agent; and where the drug is known, the technique may be used to identify the presence of a specific cell type.

The ejected particles can be observed using the methods described herein. The ejected particles can similarly be characterized by comparing the size and/or shape with a library of data collected using focused light scattering techniques on known ejected particles, and/or by binding some or all of the ejected particles to an antibody or other such molecule.

V. Detection of Microparticles Ejected from Cells

In another embodiment, the ISADe device can be used to detect particle shedding. Representative biological particles which shed smaller particles include tumors, red blood cells, white blood cells, granulocytes, platelets, monocytes, neutrophils, lymphocytes, endothelial cells, cancer cells, stem cells, bacteria, viruses, and fungi. Particle shedding may result from cell interactions, a change of cellular state such as activation or deactivation, as a result of expression, cell death, etc. The methods described herein can be used to identify such particle shedding.

In one embodiment, a drug or ligand is added to a vessel with a cell. Where the drug or ligand reacts with the cell, the cell may shed membrane particles or other particles. As described in detail herein, the method can be used to detect the size, number and/or type of particles shed by the reaction. Therefore, where the cell is known, this technique may be used to detect efficacy of unknown drug agent; and where the drug is known, the technique may be used to identify the presence of a specific cell type.

The ejected particles can be observed using the devices and methods described herein. The ejected particles can similarly be characterized by comparing the size and/or shape with a library of data collected using focused light scattering techniques on known ejected particles, and/or by binding some or all of the ejected particles to an antibody or other such molecule.

Figure 6:
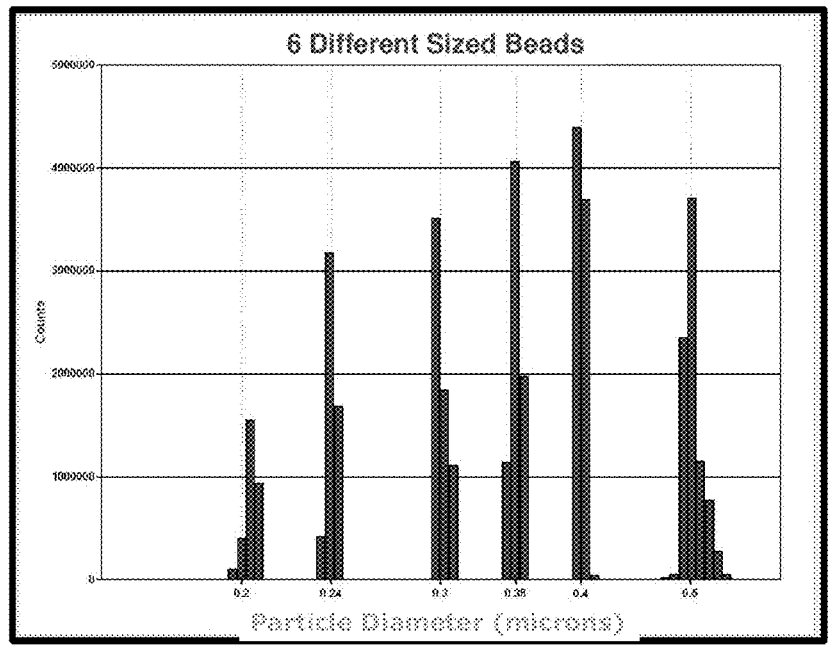
FIG. 6 is a chart showing the measurement of particles in a sample composed of 6 differently-sized polystyrene beads, assessed using the surface antigen detection enumerator light scattering device in terms of particle count (number) by particle size (μm). The chart shows the remarkable resolution of very small particle sizes. Current flow cytometers are not capable of resolution to this degree.

The ISADe device described above can be used to identify particles in the given size range (i.e., the size of the ejected (shed) microparticles and the size of the platelets). As shown in FIG. 6, a sample composed of 6 differently-sized polystyrene beads was introduced to the device, and assessed using the device in terms of particle count (number) by particle size ($\mu$m). The chart shows the remarkable resolution of very small particle sizes. Current flow cytometers are not capable of resolution to this degree.

Figure 7:
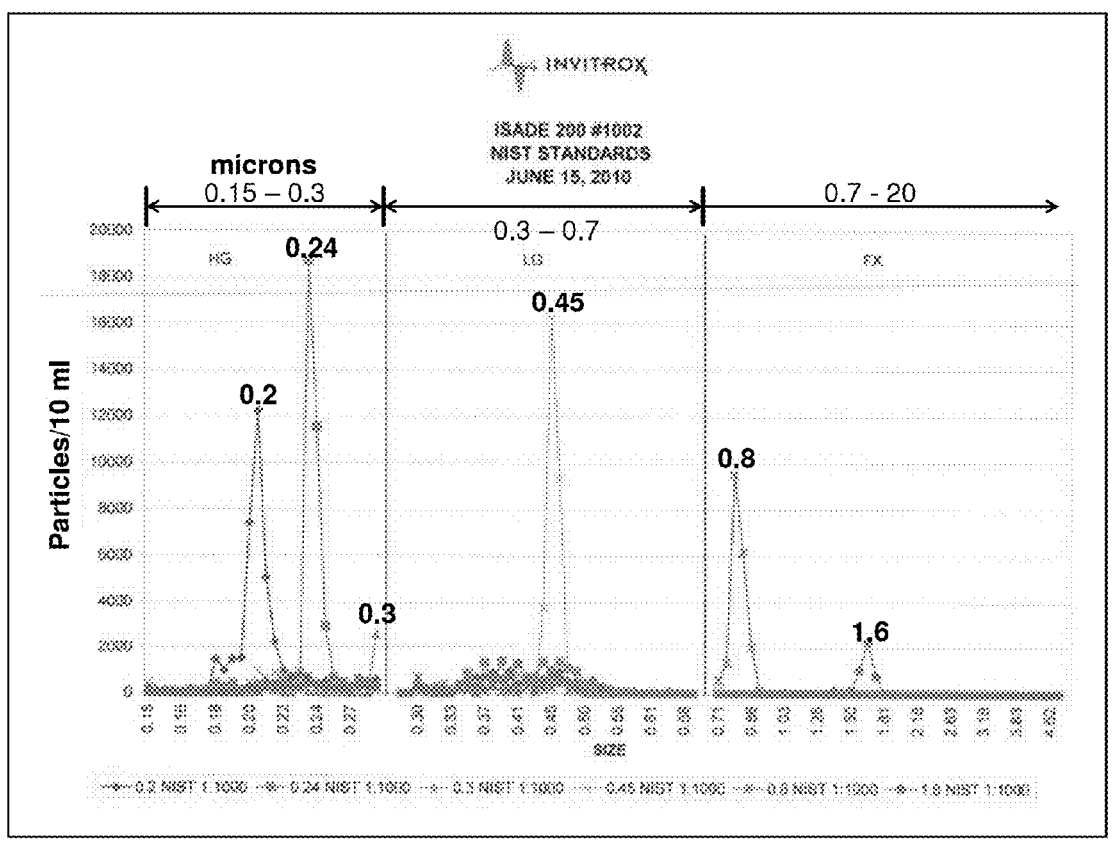
FIG. 7 is a chart showing similar data from the data shown in FIG. 6. The data in FIG. 7 is presented as points rather than as histograms, and is reflected in particles per 10 ml sample, versus particle size (μm). Also, FIG. 7 separates the size distribution into 3 different windows. In this embodiment, each window has a separate detector that has been adjusted to detect particles in a specific size range. The smallest particles are assessed from scatted light focused onto a high-gain detector, the middle window from scattered light focused onto a low gain detector, and the window with the largest particles by a light extinction method.

FIG. 7 is a chart showing similar data from the data shown in FIG. 6. The data in FIG. 7 is presented as points rather than as histograms, and is reflected in particles per 10 ml sample, versus particle size ($\mu$m). Also, FIG. 7 separates the size distribution is separated into 3 different windows. In this embodiment, each window has a separate detector that has been adjusted to detect particles in a specific size range. The smallest particles are assessed from scatted light focused onto a high-gain detector, the middle window from scattered light focused onto a low gain detector, and the window with the largest particles by a light extinction method.

Detecting Individual Molecules

In one embodiment, the methods permit one to detect the presence of specific molecules, where the molecules are of a size below the threshold limit of detection for focused light scattering techniques. In this embodiment, highly reflective metallic particles, such as gold particles, are covalently linked to a ligand that binds to the molecules of interest. Because the metallic particles are dense and highly efficient light scattering particles, the amount of light scattering when the ligand binds to a molecule of interest can be measured using the focused light scattering technique, thus confirming the presence or absence of a molecule of interest in the solution. In another embodiment, microparticles conjugated to an active agent known to bind in a specific manner to a particular species of shed particles are used, rather than metallic particles. The complex of the shed particle and the microparticle is then measured. Representative agents include antibodies and small molecules known to bind to the particular shed particles.

Detection of Particle Aggregation

In another embodiment, the method is used to determine particle aggregation and types of aggregation. Such aggregation may include, but is not limited to aggregation of a particle with other particles, or aggregation of a particle with a drug.

Particularly with respect to liposomal therapy, agglomeration of particles (such as liposomes) can result in significant mortality or morbidity when the agglomerated particles are administered. Accordingly, the method can be used to evaluate a sample of liposomes before administration to ensure that the particles have not agglomerated before a patient is treated.

VI. Methods for Detecting Binding of a Particle to a Known Molecule

In some embodiments, one knows the identity of a known molecule, for example, a drug molecule that is known to interact with the receptor on a biological particle that may or may not be present in the sample medium. By incubating the sample medium with a conjugate of the drug molecule and a microparticle, one can look for complex formation indicative of the binding of the drug molecule with biological particles in the sample medium. The complex formation can be observed over time, or simply after a suitable incubation period.

The methods can be performed by using, as a starting material, either a drug or a biological microparticle in a vessel, and then adding a known material (either a known cell or microbe, for example) to test for interaction with drug; or a known drug to test for interaction with microparticle). Then, focused light scattering techniques can be performed to look for change in particle size from size of starting material, where an increase or decrease in particle size is indicative of interaction and binding.

In order to preserve the ability of the known molecule to bind to the particle of interest, in those embodiments where a molecule is conjugated to a microparticle, it is conjugated in a way that does not adversely impact its ability to bind to the particle of interest. This may involve developing a modified molecule, wherein the molecule is modified to include a functional group capable of being conjugated to the microparticle, such that the molecule still maintains its ability to form a complex with the particle of interest. Such modifications are routine in the art.

By using a biological particle known to form a complex with the active agent, one can evaluate such modified compounds for their ability to maintain their binding affinity for the particle of interest by incubating the modified compound, or the conjugate of the compound with the microparticle with the particle. Those compounds which maintain the ability to bind the particle of interest can be identified using focused light scattering techniques, because the particle size of the complex is larger than the particle size of the non-complexed particle and non-complexed conjugate.

Column-Based Approaches to Removing Biological Particles

Rather than forming a complex of the biological particle and a conjugate of an active agent and a microparticle, one can optionally prepare a column including microparticles conjugated to agents that bind to the biological particle of interest, and pass the sample medium through a column including the microparticles. The sample, minus any complexed biological particles, will elute from the column. By performing the focused light scattering method on the eluted material, one can identify changes in particle number/population density, as compared to the starting material. A decrease in particle number/population density is indicative of interaction and binding in the column, and, therefore, an indication that the biological particle of interest was present in the sample.

Magnetic Bead-Based Approaches to Remove Biological Particles

Rather than forming a complex of the biological particle and a conjugate of an active agent and a microparticle, and using focused light scattering methods to identify the presence of the complex between the biological particle and the conjugate, one can optionally use a magnetic microparticle conjugated to the active agent. Thus, one can first obtain a focused light scattering spectra using the methods described herein, then use magnetic particles to complex with the biological particle of interest. The complex can be removed from the sample media using a magnet. Then, one can obtain a second focused light scattering spectra, and identify whether the number of biological particles of interest has been reduced.

VII. Methods for Determining Binding of a Known Particle to an Unknown Compound

In other embodiments, it is desired to learn whether a putative therapeutic agent can bind to known biological particles. In these embodiments, putative therapeutic agents are conjugated to a microparticle or metallic nanoparticle, such as a gold nanoparticle, and incubated with the known biological particles. Thus, one can determine whether a compound forms a complex with the biological particles.

In some aspects of this embodiment, it is desirable to know the minimum inhibitory concentration, or binding affinity, of an active agent. The agent can be complexed with the biological particle at differing concentrations, and this information can be obtained. Some degree of extrapolation may be required, since the agent is conjugated to a microparticle, and therefore may behave differently than the native drug.

In other aspects of this embodiment, it is desired to know the selectivity of an active agent for one receptor over another. In this aspect, the agent can be complexed with a plurality of biological particles expressing differing receptors, and binding information can be obtained for each of the receptors. Thus, selectivity can be determined.

Determining Therapeutic Activity/Efficacy/Selectivity

In another embodiment, the method is used to identify therapeutic agents. While small molecules, proteins and peptides are not likely to be large enough to see, even with this technique, they can either be coupled to a microparticle, such as a latex particle or magnetic bead, which can be incubated with the molecules, or placed on a column.

In one aspect of this embodiment, a biological particle with a target for the therapeutic agent (i.e., a receptor) is placed in suspension, and microparticles conjugated to one or more putative therapeutic agents are added to the suspension.

If the therapeutic agent binds to the biological particle, the binding can be observed because the size of the complex of the biological particle and the conjugate is greater than that of the conjugate or the biological particle.

This technique can be used, for example, to determine the efficacy of specific antibacterial or other drug candidates for a particular infection, or to identify agents useful for treating specific types of cancer. In one aspect of this embodiment, the techniques are useful for personalized medicine, where a particular patient's bacterial infection, platelet or cancer cells, or erythrocytes, are analyzed for their ability to bind to and interact with specific therapeutic agents. In another aspect of this embodiment, one can generate a plurality of spectra and compare the results, to determine minimum inhibitory concentrations and, therefore, useful dosage ranges for a given drug (where the drug is an inhibitor).

VIII. Methods for Identifying Patients Likely to Benefit from Treatment

Certain patients respond to therapy due to an interaction of a cellular receptor with a drug molecule. However, certain other patients have genetic mutations which do not permit the patients cells to bind to the drug molecule, thus rendering the drug ineffective. To determine whether a patient will respond to a given therapy, a solution of the patient's cells can be combined with a drug molecule of interest, where the molecule is bound to a probe particle, which can be a microparticle or nanoparticle. If the drug molecule of interest binds to the patient's cells, then the concentration of the conjugate, and/or the patient's cells will be lower, and a new peak corresponding to the complex of the cells and the conjugate will be observed. The absence of a new peak corresponding to the complex of the cells and the conjugate is indicative that the patient will not respond to the particular drug therapy. Thus, the method can confirm that the patient will or will not achieve a benefit using the particular drug therapy. This enables a personalized medicine approach using rapid and inexpensive methods.

In one aspect of this embodiment, the cells are cancer cells from an individual patient, and sample media containing the cancer cells are incubated with a series of therapeutic agents bound to a microparticle or nanoparticle. Those therapeutic agents that form a complex with the cancer cells are potential candidates for personalized treatment of the patient, since they bind to and interact with the cancer cells. This technique can provide a relatively quick and inexpensive method for identifying patients who have certain mutations, such as HER2 positive patients, patients whose cancer cells have vitamin D receptors, patients with estrogen-responsive cancer cells, and the like.

In another aspect of this embodiment, the cells are blood cells from a patient suffering from atherosclerosis, and who is being evaluated to see if his blood cells will respond to treatment with clopridogrel bisulfate (Plavix®). The interaction with the blood cells and clopidogrel bisulfate is a surface interaction, but a small percentage of patients have a mutation in their blood cells that inhibits the surface interaction with this compound. For most of those patients, there is an alternative therapeutic agent, but it is important to identify those patients before the symptoms worsen, possibly leading to a heart attack. In this aspect, blood cells of a patient are incubated with microparticles conjugated to clopidogrel bisulfate, and a spectrum is obtained using focused light scattering techniques. For example interaction of the probe particle can be between the ADP receptor and Plavix target, P2Y12 or to the activation of the of VASP pathway. The presence of a complex between the clopidogrel bisulfate and the blood cells can be observed. Further, if the patient is responsive to Plavix, no activation will occur when ADP or other specific agonists are added to the patient's platelets. Thus, no activation will occur and specific activation epitopes, like CD62, glycoprotein alpha2, beta3, etc., will be detected by specific probe particles. Because the size of blood cells and the microparticle/clopidogrel bisulfate conjugate are known, only one spectrum needs to be obtained, and the only peak of interest is the peak corresponding to the complex of the conjugate with the blood cells.

IX. Methods for Performing High Throughput Bioassays

Any and all of these assays can be optimized for high throughput screening using suitable robotics. Liquid handlers can transfer samples to a multi-tube or multi-well plate, and a "memory map" can be used to correlate the samples to their location on the plate. Information on each sample can then be stored, and used to provide information about drug candidates, patient diagnoses, and proposed patient treatment options.

Robotics systems are known in the art, and can be used to move samples taken from individual patients to known positions in a multi-tube or multi-well plate. Once information on the sample is obtained using the focused light scattering techniques described herein, the information can be correlated to the individual patient via the stored information correlating the location of the tube and the patient identification. Liquid handlers can take portions of the sample and evaluate a plurality (i.e., at least two) of different screening assays, for example, by incubating portions of the sample with different microparticles, bound to different active agents.

Automated processes using known robotics can be used to pull and place samples (like high throughput screening) with use of a "memory map". A user can then pick desired screens to be run and the robotic apparatus will implement desired processes.

In another aspect of the embodiments described herein, the methods can be automated using robotics to pull and place samples (analogous to conventional high throughput screening methods), optionally in conjunction with a "memory map". A user can then pick desired screens to be performed, and the robotic apparatus can implement the desired processes. In this embodiment, a laboratory can be set up to automatically screen numerous samples.

In a preferred embodiment, the personalized medicine processes described herein are automated, to provide relatively inexpensive, and relatively fast, high throughput screening methods to identify preferred therapies for patients suffering from disease.

X. Reference Libraries

A reference database of information gained by performing focused light scattering on known compounds can be used. One can compare the sample to the reference database in order to identify or characterize the particles in the tested sample. A reference database includes at least two, preferably more than ten, more preferably greater than a hundred, and most preferably, greater than a thousand bits of information on particle size that can be used to correlate the particle size measured using the techniques described herein with particle sizes for known biological particles that are stored in the reference database.

The present invention will be better understood with reference to the following non-limiting examples.

Example 1

Representative Focused Light Scattering Device

A representative focused light scattering device is shown in FIG. 1. A first laser (1) emits light at a first wavelength, and a second laser (2) emits light at a second wavelength. Both beams of light pass through a first beam splitter (3) and through a first focusing lens (4) before they enter into a flow cell (15). The flow cell includes a site (5) for hydrodynamic injection of the sample. As the platelets in the flow cell pass through the beams of light, the light is scattered as it hits the platelets. The scattered light passes through a circular spatial filter (6) and then through a first collimating lens (7). The light beam passes through a second beam splitter (16), which splits the light into two beams. A first beam passes through a second focusing lens (8) and through a first chromatic filter (9) that passes scattered light from the first laser (1) through a first detector (10). The second beam passes through a second collimating lens (11), a third focusing lens (12) and a second chromatic filter (13) that passes scattered light from the second laser (2) to a second detector (14).

The two photodetectors (10 and 14) each are able to detect light at a certain frequency, so that light transmitted at different frequencies (as a result of the two lasers hitting particles, and which may interact with fluorescent tags on the particles) can be separately determined.

A third detector (an extinction detector) (18) receives a portion of the light passing through the flow cell. A portion of the light passing through the flow cell is reflected off of a movable mirror (17) and onto the third detector.

Example 2

Detection of Microparticle's (MP) Present in a Biological Sample

In this example, a specimen is subject to particle sizing and counting. After an appropriate dilution of the sample, the diluted specimen is introduced into the device for analysis. As counting proceeds, counts will accumulate in the size region less that 1 micron. The appearance of MP in this size region will indicate the presence of MPs.

Example 3

Microparticle Characterization

Once MPs are detected, as described in Example 2, it may be important to determine the source of the MP (from platelets neutrophils, tumor cell, etc.). This Example provides two different options for characterizing the MP.

The first option is to use MP sizing and counts. In this case, the specimen is incubated with a second particle with a specific ligand conjugated to its surface. The choice of the ligand will depend on the specific MP be characterized. For example, if the MP of interest has coagulation tissue factor (TF) on its surface, the conjugated particle can be conjugated with an antibody against TF-particle or with coagulation factor FVII. Either ligand will specifically bind to MPs with TF on their surfaces.

When the conjugated particles are incubated with the anti-TF conjugated particles, a new size corresponding to the TF-MP+anti-TF-particles will appear when the MP and the probe particle are counted. In a like manner, other MPs can be characterized by developing probe particles with a conjugated ligand specific for the MP of interest.

The second option is to use an EQELS device to analyze the MPs. The basic procedure is the same, except that differences in the particles electrophoretic mobility can be analyzed.

Specifically, a baseline electrophoretic mobility of the MP can be obtained. The MP will then be mixed with the probe particle that is conjugated with the specific ligand for the MP of interest, or just with the ligand without conjugation to a probe particle. When the probe particle binds to the MP of interest, a difference in the electrophoretic mobility is observed. These data will provide a specific identification of the MP. If the ligand alone was used to bind to the MP, the EQELS data, in addition to IP of the particle, will also provide binding constants for the ligand to the MP.

Example 4

Determination of Cellular Activation

In this Example, the cellular activation, such as platelet activation, is determined. A baseline resting platelet run on the sizing-counting device is determined. The platelet or cell is then activated using appropriate agonists. Once activation occurs, new surface epitopes appear on the surface. In the case of the platelet DC62, CD41, various integrins, and the like, begin to appear.

A probe particle with a ligand for the specific epitope of interest is then added to the activated platelets (or other cells). The ligand can be an antibody, or small molecule, that specifically binds to the activated epitope. When binding occurs, a particle is created (the activated cell+the probe particle) which has a larger size than either the activated cell or the probe particle. The appearance of these new particles represents the appearance of the activated platelet+the bound probe particle.

Example 5

Microbe Identification

In this Example, microbes are identified using the techniques described herein. The microbe may be bacterial, viral, fungal, or protozoa. A sample containing a microbe is analyzed using the counting/sizing device described herein. The sample can be from a water supply, from a patient (human or animal), or other source. The size distribution will be determined, and compared to a database, to determine whether one or more of the particles in the sample fall into any of the sizes typical for known microbes. If so, a probe particle conjugated with a ligand that specifically binds to certain microbes can be added. The identity of the microbe is confirmed when a new size distribution is obtained when the sample is incubated with the probe particle.

Additional verification can be obtained if the specimen is examined by EQELS, where a swim rate is determined for flagellated organisms using the velocimetry mode of the EQELS device. The EQELS device can also determine the microbe's electrophoretic mobility. This information can be compared with data in an EQELS database for further confirmation of the identity of the particle.

If indicated, EQELS will then be used to help determine the appropriate antimicrobial (antibiotic, antiviral, etc) agent. A know concentration of antimicrobial agent will be added to the specimen. Binding of the agent to the microbe will be determined by a change in the microbe's electrophoretic mobility. Further, if the drug kills the microbe, its surface charge density changes resulting in a rather large change in the killed microbe's electrophoretic mobility.

Example 6

Drug Efficacy: Effectiveness of Cell Inhibition

Specific Example of Aspirin or/and P2Y12 Inhibition of Platelet Activation

Platelet inhibition in arterial thrombophilic diseases is considered the standard of care. Unfortunately, in some patients, conventional drugs do not inhibit the patient's platelets. Approximately 25% of ASA-treated and 29% of Plavix-treated patients do not respond to treatment. Currently, there is no accepted assay to identify the resistant/refractory patients.

The assay described herein can use particle sizing, based on the following concept, to identify resistant/refractory patients. The goal of treatment with anti-platelet drugs is to inhibit activation. When the platelet is activated, new surface epitopes appear. So, in this embodiment, the patient's platelets are first obtained as platelet rich plasma (PRP). A baseline measurement of the particle size and/or distribution is then made. Next, an aliquot of the patient PRP can be mixed with a platelet activator (agonist). If the drug works, no activation occurs. If it does not work, the platelet will activate. The assay can then probe the platelet surface for the appearance of new epitopes like CD62, CD41 and the like. The surface can be probed with a ligand (antibody or otherwise) that is conjugated to a particle. If binding occurs, the probe particle will bind with the activated platelet, and a particle with a different (larger) particle size (i.e., the activated platelet+conjugated-probe particle) will appear. If the drug works, no change in the particle size distribution will occur.

Example 7

Lipid Droplets as Drug Delivery Vehicles

Certain sized particles do not perfuse capillaries well. Since a typical capillary is approximately 2-3 microns in diameter, particles larger that that size must have a surface to volume ratio that will permit the distortion of the particle so that is can enter the capillary system; similar to a red blood cell. In this Example, particle sizing is used to identify particles which fall into a range that will not be perfused, and result in potential malaise or death to the patient. Further, the surface characteristics of some particles lead to instability, that may cause particle aggregation or fragmentation. Similar problems are well recognized in colloidal chemistry.

In this embodiment, drugs like Ambisome™, Daunosome™, Doxil™, or other liposomal drug delivery vehicles, can be screened for a safe particle size distribution prior to infusion. The screen can identify particles by particle size and distribution, so if relatively large particles, corresponding to agglomerated liposomal or other particles are observed, then the sample can be rejected before being infused. Alternatively, the sample can be subjected to conditions which de-agglomerate the particles (for example, ultrasound and the like), and the sample re-tested. These assays can also be used to optimize the solution, and particle surface optimization for identifying the best lead compound(s).

Example 8

Small Molecule Distribution Assays. Specific Examples of vWF or Serum Plasma vWF is a polydispersed molecule with a molecular weight distribution range of 500,000 to 20 million or even higher. Thus, there is a substantial difference in the molecular size distribution. Current technology requires a minimum of several days to complete an analysis.

In this embodiment, gold beads are conjugated with an anti-vWF antibody in a manner that would bind one bead to one vWF multimer. Since the mass density of the gold bead results in more efficient light scattering, vWF molecules bound to the gold beads will be visible to the focused scattering sizing and counting device. Thus, the presence of, and in some embodiments, the amount of, vWF can be determined.

Accordingly, although the invention has been described herein with reference to various illustrative aspects, features and embodiments, it will be recognized that the invention is not thus limited, but rather extends to and encompasses other variations, modifications and alternative embodiments, such as will suggest themselves to those of ordinary skill in the art, based on the disclosure herein. The claims hereafter set forth therefore are intended to be broadly construed and interpreted as including all such variations, modifications and alternative embodiments within their spirit and scope.

The invention claimed is:

1. A device for measuring the size and/or number of particles in a sample medium, comprising:
    a) two or more lasers which produce two or more beams of laser light;
    b) a beam splitter that combines the two or more beams of laser light from the two or more lasers, thereby forming a combined beam of laser light, and passes the combined beam of laser light through a first focusing lens, the first focusing lens focuses the combined beam of laser light such that an effective width of the combined beam of laser light in a direction transverse to the path of the combined beam of laser light is between about 0.05 and 0.5 μm, thereby forming a first focused beam of laser light;
    c) a flow cell positioned in the path of the first focused beam of laser light, wherein the flow cell is adapted to receive and pass the sample medium comprising a dispersion of the particles, and passing the sample medium through the first focused beam of laser light, so that the first focused beam of laser light is scattered when it interacts with one or more of the particles, thereby forming scattered beams of laser light, and the first focused beam of laser light is not scattered if it does not interact with one or more of the particles, depending on whether the one or more particles are in the path of the first focused beam of laser light;
    d) a mirror positioned between the flow cell and a spatial filter, to reflect a portion of the scattered beams of laser light, thereby forming reflected scattered light, and
    e) an extinction detector positioned in the path of the reflected scattered light;
    f) the spatial filter positioned in the path of the scattered beams of laser light; allows the scattered beams of laser light to pass through, and does not allow the first focused beams of laser light that are not scattered to pass through;
    g) a first collimating lens positioned in the path of the scattered beams of laser light that passed through the spatial filter, to collimate the scattered beams of laser light that passed through the spatial filter, thereby forming a first collimated beam of laser light;
    h) a second beam splitter positioned between the first collimating lens and a second collimating lens, to split the first collimated beam of laser light into a first beam of laser light and a second beam of laser light, wherein the first beam of laser light is not diverted from an original path toward a second focusing lens, and the second beam of laser light is diverted from the original path toward the second focusing lens onto a second path, thereby forming a diverted beam of laser light,
    the second collimating lens positioned along the second path, for collimating the diverted beam of laser light, thereby forming a second collimated beam of laser light,
    the second focusing lens positioned in the path of the first beam of laser light, for focusing the first beam of laser light, thereby forming a second focused beam of laser light;
    i) a scatter detector positioned in the path of the second focused beam of laser light.

2. The device of claim 1, further comprising a first chromatic filter between the second focusing lens and the scatter detector.

3. The device of claim 1, further comprising a third focusing lens positioned in the path of the second collimated beam of laser light for focusing the second collimated beam of laser light, thereby forming a third focused beam of laser light.

4. The device of claim 3, further comprising a second chromatic filter, positioned in the path of the third focused beam of laser light.

5. The device of claim 4, further comprising a detector positioned in the path of the third focused beam of laser light that passed through the second chromatic filter.

6. The device of claim 5, wherein the detector is a fluorescence detector.

7. The device of claim 1, further comprising: a processor adapted to receive information from the extinction detector and/or scatter detector, and to responsively generate an output correlative of the size and/or number of particles in the sample medium.

8. The device of claim 1, wherein the device comprises three or more lasers.

9. The device of claim 8, further comprising a separate detector, beam splitter, collimating lens, and/or focusing lens for the third laser, and one additional detector, beam splitter, collimating lens, and/or focusing lens for each additional laser over three.

10. A method of identifying a biological particle of interest in a sample medium, said method comprising:
    a) introducing the sample medium, which may or may not include the biological particle of interest, into the device of claim 1;

b) using focused laser light scattering techniques to prepare a spectrum showing particle size distribution within the sample medium; and
c) identifying the presence or absence of the biological particle of interest by comparing the particle size distribution within the sample medium with a known size of the biological particle of interest.

11. The method of claim 10, wherein, after an initial determination is made that the biological particle of interest is present in the sample medium, a confirmatory assay is performed.

12. The method of claim 10, wherein the biological particle of interest is selected from the group consisting of tumor cells, red blood cells, white blood cells, granulocytes, platelets, monocytes, neutrophils, B-cells, T-cells, lymphocytes, erythrocytes, cancer cells, stem cells, bacteria, viruses, protozoa and fungi.

13. A method of determining the efficacy of a putative therapeutic agent, comprising:
a) obtaining a first spectra showing particle size and distribution using focused light scattering techniques on a sample medium comprising a biological particle with a receptor to which the putative therapeutic agent will bind, using the device of claim 1;
b) incubating the sample medium with the putative therapeutic agent;
c) obtaining a second spectra showing particle size and distribution on the incubated sample medium using the focused light scattering techniques; and
d) determining whether the particle size and distribution has been altered by the incubation of the putative therapeutic agent by comparing the first spectra and the second spectra, wherein a change in the particle size and/or distribution following the incubation step is indicative of a complex formation of the putative therapeutic agent and the biological particle.

14. The method of claim 13, wherein the putative therapeutic agent is conjugated to a microparticle, such that there is a measurable size difference between the biological particle not complexed with the putative therapeutic agent and the complex of the putative therapeutic agent and the biological particle.

15. A method for determining whether a biological particle will form a complex with a known therapeutic agent, comprising:
a) obtaining a first spectra showing particle size and distribution using focused light scattering techniques on a sample medium comprising the biological particle with a receptor to which the known therapeutic agent may or may not bind, using the device of claim 1;
b) incubating the sample medium with the known therapeutic agent;
c) obtaining a second spectra showing particle size and distribution on the incubated sample medium using the focused light scattering techniques; and
d) determining whether the particle size and distribution has been altered by the incubation of the known therapeutic agent by comparing the first spectra and the second spectra, wherein a change in the particle size and/or distribution following incubation is indicative of a complex formation of the known therapeutic agent and the biological particle.

16. A method of detecting particle shedding resulting from a cell interaction, comprising:
a) generating a first spectrum showing particle size and distribution, using focused light scattering techniques, for a known cell in a sample medium; using the device of claim 1;
b) incubating a potential therapeutic agent with the known cell in the sample medium, wherein the potential therapeutic agent is a microparticle;
c) generating a second spectrum showing particle size and distribution, using the focused light scattering techniques, for the incubated sample medium;
d) comparing the first and second spectra, wherein the presence of, or increase in particle density of, particles of a size less than those of the known cell is indicative of the particle shedding.

17. A method of identifying particle aggregation in a sample medium, comprising:
a) generating a first spectrum showing particle size and distribution, using focused light scattering techniques, for the sample medium comprising a biological particle, using the device of claim 1,
wherein the presence of a peak corresponding to a particle size of aggregated particles is indicative of the presence of an aggregate.

18. The method of claim 17, further comprising incubating the sample medium with an active agent which promotes or inhibits the particle aggregation in the absence of a specific mutation in the biological particle,
wherein development of, or lack of development of, the particle aggregation provides information on activity, or lack of activity, of the active agent against the biological particle.

19. The device of claim 1, wherein the device further comprises a hydrodynamic flow injector for introducing the sample medium into the flow cell.

* * * * *